(12) United States Patent
Mertens et al.

(10) Patent No.: US 10,299,983 B2
(45) Date of Patent: May 28, 2019

(54) SYSTEMS AND METHODS FOR THERAPEUTIC TREATMENTS OF VARIOUS CONDITIONS OF A FEMALE PERSON

(71) Applicant: OHMEA MEDICAL TECHNOLOGIES LLC

(72) Inventors: Jane Mertens, Del Mar, CA (US); Dean P. Bauer, Del Mar, CA (US); Yuval Shenkal, Cardiff-By-The-Sea, CA (US); Harvey W. Starr, San Diego, CA (US)

(73) Assignee: OHMEA MEDICAL TECHNOLOGIES LLC, Del Mar, CA (US)

( * ) Notice: Subject to any disclaimer, the term of this patent is extended or adjusted under 35 U.S.C. 154(b) by 831 days.

(21) Appl. No.: 14/670,198

(22) Filed: Mar. 26, 2015

(65) Prior Publication Data
US 2015/0196455 A1 Jul. 16, 2015

Related U.S. Application Data

(63) Continuation of application No. 13/667,938, filed on Nov. 2, 2012, now Pat. No. 9,011,316.
(Continued)

(51) Int. Cl.
*A61H 19/00* (2006.01)
*A61H 7/00* (2006.01)
(Continued)

(52) U.S. Cl.
CPC ............. *A61H 19/40* (2013.01); *A61H 7/007* (2013.01); *A61H 9/0057* (2013.01); *A61H 19/34* (2013.01);
(Continued)

(58) Field of Classification Search
CPC ....... A61H 19/34; A61H 7/007; A61H 9/0057
(Continued)

(56) References Cited

U.S. PATENT DOCUMENTS

| 1,858,209 A | 5/1927 | Lang |
| 1,964,590 A | 11/1931 | Muller |

(Continued)

OTHER PUBLICATIONS

"Berman et al. Female sexual dysfunction: anatomy, physiology, evaluation and treatmentoptions. Curr Opin Ural. 1999; 9:563-568."
(Continued)

*Primary Examiner* — Samuel G Gilbert
(74) *Attorney, Agent, or Firm* — Veros Legal Solutions, LLP

(57) ABSTRACT

Systems and methods for interactive treatments of female sexual disorders are presented. A programmable sexual stimulation device is provided, which transmits and receives data relating to the use and function of the device. The sexual stimulation device may be programmed to implement a particular combination of mechanical actions which have been customized by a user or a health care professional involved in the treatment or preference of the user. The device may also collect data on the type of mechanical actions input by the user and transmit the data to a remote location for viewing by the user or the healthcare professional. The device may also communicate with external devices which aid in the treatment programs, such as audio or image display devices which can coordinate the function of the sexual stimulation device with the presentation of audio or visual information to provide additional sources of sexual arousal to the user.

10 Claims, 19 Drawing Sheets

Related U.S. Application Data

(60) Provisional application No. 61/556,131, filed on Nov. 4, 2011.

(51) Int. Cl.
*A61H 9/00* (2006.01)
*A61H 23/02* (2006.01)
*G06F 19/00* (2018.01)

(52) U.S. Cl.
CPC ..... *A61H 23/0245* (2013.01); *A61H 23/0263* (2013.01); *G06F 19/3418* (2013.01); *G06F 19/3481* (2013.01); *A61H 7/002* (2013.01); *A61H 2201/0111* (2013.01); *A61H 2201/0188* (2013.01); *A61H 2201/0207* (2013.01); *A61H 2201/1215* (2013.01); *A61H 2201/149* (2013.01); *A61H 2201/169* (2013.01); *A61H 2201/1692* (2013.01); *A61H 2201/501* (2013.01); *A61H 2201/5007* (2013.01); *A61H 2201/5012* (2013.01); *A61H 2201/5015* (2013.01); *A61H 2201/5038* (2013.01); *A61H 2201/5046* (2013.01); *A61H 2201/5048* (2013.01); *A61H 2201/5097* (2013.01); *A61H 2205/087* (2013.01); *A61H 2230/00* (2013.01); *A61H 2230/06* (2013.01); *A61H 2230/30* (2013.01); *A61H 2230/50* (2013.01)

(58) Field of Classification Search
USPC .................................................. 600/38–41
See application file for complete search history.

(56) References Cited

U.S. PATENT DOCUMENTS

| | | | |
|---|---|---|---|
| 2,076,410 A | 4/1935 | McGerry | |
| 2,154,427 A | 10/1935 | Andres | |
| 2,314,590 A | 8/1940 | McCarty | |
| 2,234,102 A | 3/1941 | Andres | |
| 2,728,338 A | 7/1953 | Force, Jr. | |
| 4,846,159 A | 7/1989 | Anzai et al. | |
| 5,421,808 A * | 6/1995 | Osbon | A61F 5/41 600/38 |
| 5,577,997 A | 11/1996 | Thariani et al. | |
| 5,684,722 A | 11/1997 | Thorner et al. | |
| 5,902,293 A | 5/1999 | Liu | |
| 5,963,002 A | 10/1999 | Hartov | |
| 6,028,531 A | 2/2000 | Wanderlich | |
| 6,032,313 A | 3/2000 | Tsang | |
| 6,099,463 A | 8/2000 | Hockhalter | |
| 6,190,307 B1 | 2/2001 | Tsai | |
| 6,368,268 B1 | 4/2002 | Sandvick et al. | |
| 6,436,029 B1 | 8/2002 | Benderev | |
| 6,592,516 B2 | 7/2003 | Lee | |
| 6,599,236 B1 | 7/2003 | Castro | |
| 6,733,438 B1 | 5/2004 | Dann et al. | |
| 6,793,619 B1 | 9/2004 | Blumental | |
| 7,341,566 B2 | 3/2008 | Nan | |
| 7,347,815 B2 | 3/2008 | Servanescu | |
| 7,438,681 B2 | 10/2008 | Kobashikawa et al. | |
| 7,452,326 B2 | 11/2008 | Fladl et al. | |
| 7,527,589 B2 * | 5/2009 | Squicciarini | A61F 2/26 600/39 |
| 7,577,476 B2 | 8/2009 | Hochman et al. | |
| 7,608,037 B2 | 10/2009 | Levy | |
| 7,628,744 B2 | 12/2009 | Hoffman et al. | |
| 7,715,789 B2 | 5/2010 | Park et al. | |
| 7,749,178 B2 | 7/2010 | Imboden et al. | |
| 7,762,945 B2 | 7/2010 | Blumenthal | |
| 7,803,126 B2 | 9/2010 | Nan | |
| 7,815,582 B2 | 10/2010 | Imboden et al. | |
| 7,938,789 B2 | 5/2011 | Imboden et al. | |
| 7,946,977 B2 | 5/2011 | Klearman et al. | |
| 7,967,740 B2 | 6/2011 | Mertens et al. | |
| 8,012,082 B1 | 9/2011 | Lefew | |
| 8,092,403 B2 | 1/2012 | Nan | |
| 8,152,746 B2 | 4/2012 | Nan | |
| 8,255,299 B2 | 8/2012 | Cambridge | |
| 8,294,749 B2 | 10/2012 | Cable | |
| 2002/0058892 A1 | 5/2002 | Young | |
| 2002/0120219 A1 * | 8/2002 | Hovland | A61F 5/48 601/6 |
| 2002/0133103 A1 | 9/2002 | Williams et al. | |
| 2002/0156404 A1 | 10/2002 | Kuo | |
| 2003/0036678 A1 | 2/2003 | Abbassi | |
| 2004/0010328 A1 | 1/2004 | Carson et al. | |
| 2004/0030273 A1 | 2/2004 | Tucker | |
| 2004/0097852 A1 | 5/2004 | Boyd et al. | |
| 2005/0075072 A1 | 4/2005 | Apitzsch | |
| 2006/0116612 A1 | 2/2006 | Drysdale | |
| 2006/0069329 A1 | 3/2006 | Nan | |
| 2006/0100555 A1 | 5/2006 | Cagle et al. | |
| 2006/0106466 A1 | 5/2006 | Decker et al. | |
| 2006/0247561 A1 | 11/2006 | Chiu | |
| 2006/0270897 A1 * | 11/2006 | Homer | A61H 19/00 600/38 |
| 2007/0055096 A1 | 3/2007 | Berry et al. | |
| 2007/0100259 A1 | 5/2007 | Nan | |
| 2007/0118058 A1 | 5/2007 | Isshiki | |
| 2007/0244416 A1 | 10/2007 | Sobin et al. | |
| 2008/0071138 A1 * | 3/2008 | Mertens | A61H 7/005 600/38 |
| 2008/0119767 A1 | 5/2008 | Berry et al. | |
| 2008/0147684 A1 | 6/2008 | Sadovsky et al. | |
| 2008/0208086 A1 | 8/2008 | Wu | |
| 2009/0012434 A1 | 1/2009 | Anderson | |
| 2009/0099413 A1 | 4/2009 | Kobashikawa et al. | |
| 2009/0171144 A1 | 7/2009 | Squicciarini | |
| 2010/0087757 A1 | 4/2010 | Hoffman et al. | |
| 2010/0174135 A1 | 7/2010 | Shim | |
| 2010/0174213 A1 | 7/2010 | Shim | |
| 2010/0191048 A1 | 7/2010 | Kulikov | |
| 2010/0262049 A1 | 10/2010 | Novak et al. | |
| 2011/0218395 A1 | 9/2011 | Stout | |
| 2012/0157893 A1 | 6/2012 | Fang | |
| 2012/0179077 A1 | 7/2012 | Tuck et al. | |
| 2012/0215141 A1 | 8/2012 | Peddicord | |

OTHER PUBLICATIONS

"Billups et al. A new non-pharmacological vacuum therapy for female sexual dysfunction.Journal of Sex & Marital Therapy. 2001; 27:435-441.".
"Billups, K. L. The role of mechanical devices in treating female sexual dysfunction andenhancing the female sexual response. World J Urol. 2002; 20:137-141."
"Bultrini et al. Possible correlation between type 1 diabetes mellitus and female sexualdysfunction: case report and literature review. J Sex Med. 2004; 1 :337-340."
Doruk et al. Effect of diabetes mellitus on female sexual function and risk factors. Archives of Andrology. 2005; 51:1-6.
Extended European search report for PCT/US2007/077293, dated Nov. 2012.
"Harvard Men's Health Watch. Pills and Potency: Blood pressure drugs and sexualdysfunction. Feb. 1999; 7-8."
International search report for PCT/US2012/063348, dated Mar. 18, 2013.
"Okeahialam et al. Sexual dysfunction in female hypertensives. Journal of the National MedicalAssociation. 2006; 98(4):638-640."
"Park et al. Diabetes induced alteration of clitoral hemodynamics and structure in the rabbit.The Journal of Urology. 2002; 168:1269-1272."
Schroder et al. Clitoral therapy device for treatment of sexual dysfunction in irradiated cervical cancer patients. Int J Radiation Oncology Bioi Phys. 2005; 61(4)1078-1086.
"Story, N.L. Sexual dysfunction resulting from drug side effects. The Journal of Sex Research.1974; 10(2):132-149."

(56) References Cited

OTHER PUBLICATIONS

"Wilson et al. Treating symptoms of female sexual arousal disorder with the Eros-ClitoralTherapy Device. J Gend Specif Med. 2001; 4(2):54-58."

\* cited by examiner

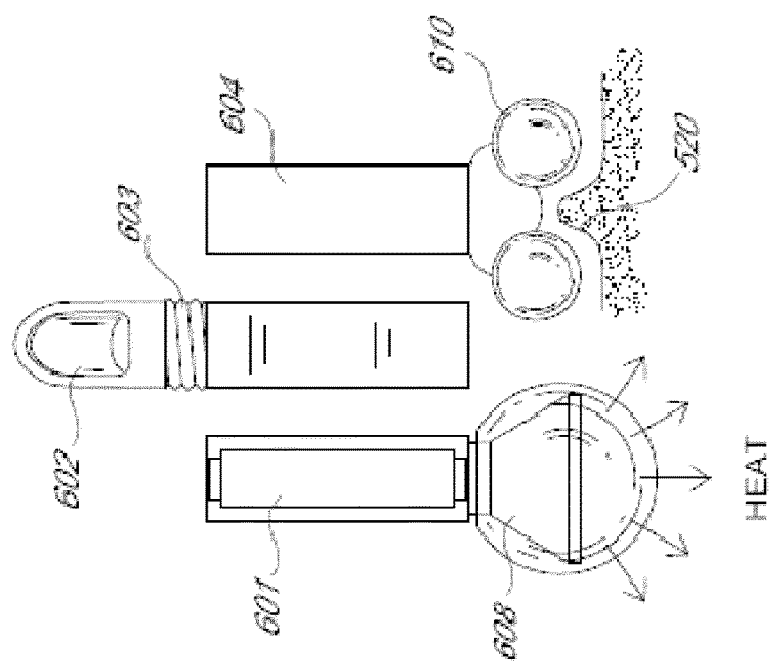
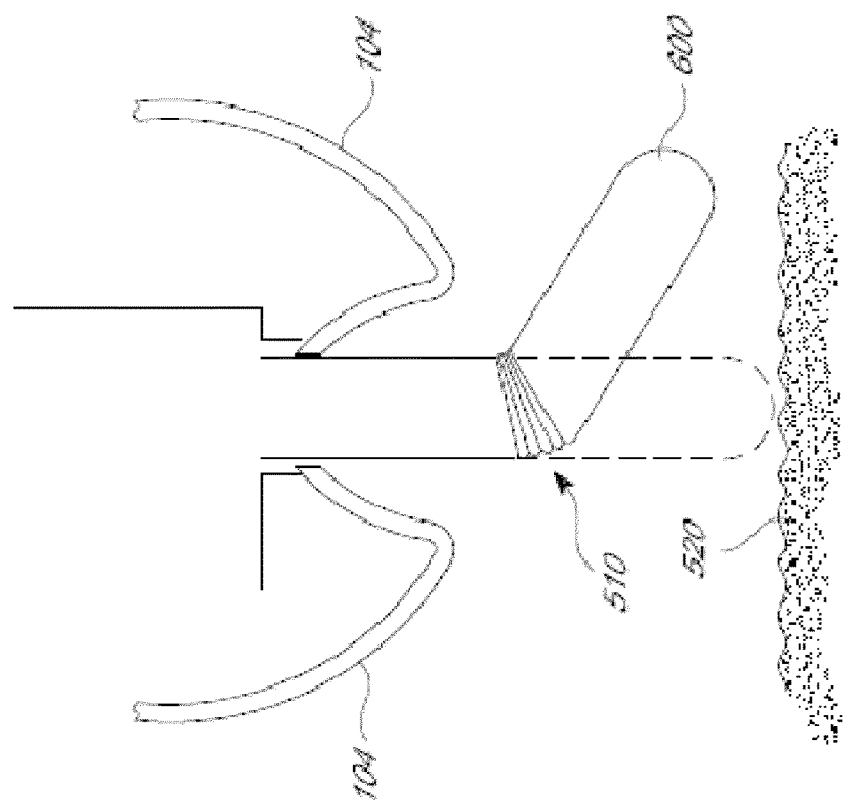
FIG. 5D

SYSTEMS AND METHODS FOR THERAPEUTIC TREATMENTS OF VARIOUS CONDITIONS OF A FEMALE PERSON

CROSS-REFERENCE TO RELATED APPLICATIONS

This application is a continuation of U.S. patent application Ser. No. 13/667,938, filed on Nov. 2, 2012, which claims priority to U.S. Provisional Application 61/556,131, filed on Nov. 4, 2011. The entire disclosure of these applications including the appendices is hereby incorporated by reference.

BACKGROUND OF THE INVENTION

Field of the Invention

This invention relates to systems and methods for treating various conditions of a female patient in need thereof, the conditions being female sexual dysfunction and urinary incontinence, and more specifically to a programmable sexual stimulation device which transmits and receives data relating to the use and function of the device.

Description of the Related Art

The Diagnostic and Statistical Manual of Mental Disorders (DSM-IV-TR) identifies sexual dysfunctions as sexual desire disorders, sexual arousal disorders, orgasmic disorders, and sexual pain disorders (with or without being due to a medical condition).

Statistical estimates vary greatly, but it is thought that the overall prevalence of female orgasmic disorders may be up to 76% of all women (Berman et al., Curr Opin Urol. November 1999; 9(6):563-8).

Certain physical conditions which cause decreased blood supply which may interfere with or prevent a female from achieving clitoral tumescence and is impactful in controlling orgasmic ability. Several medical conditions, such as diabetes, atherosclerosis, and thyroid disorders, have been shown to negatively impact orgasmic ability (Bultrini et al., J Sex Med. November 2004; 1(3):337-40; Dorurk et al., Arch Androl. January-February 2005; 51(1):1-6). Additionally, many medications themselves also have the potential to inhibit orgasmic ability, such as some blood pressure medicines and anti-depressants (Okeahialam et al., J Natl Med Assoc. April 2006; 98(4):638-40; Harv Mens Health Watch. February 1999; 3(7):7-8; Story, J Sex Res. May 1974; 10(2):132-49).

Researchers have been cognizant of the observations that the above identified conditions and medicaments may result in decreased or hindered blood flow to the clitoral region of females, thus causing or, at a minimum, exacerbating such problems (Berman et al., Curr Opin Urol. November 1999; 9(6):563-8; Park et al., J Urol. September 2002; 168(3): 1269-72).

The female sexual response cycle is divided into four phases: (1) excitement; (2) plateau; (3) orgasm; and (4) resolution. The device of the present invention is intended to focus specifically on the most difficult transition, namely from plateau to orgasm.

The clitoris is the most sensitive sexual body part. It is the only organ in the human body to have no other function than to provide pleasure. The clitoris is comprised of the external glans (head), protected by a hood, the shaft (continuing towards the pubic bone), and two "legs" (crura) that are internal and surround the vaginal opening in a V-shape. Typically, the general reference to the clitoris usually means the glans. The body of the clitoris refers to the internal portion.

During orgasm, the clitoris becomes engorged and enlarged from increased blood supply and then pulls under the hood of the clitoris prior to orgasm.

A variety of mechanical approaches have been developed to enhance sexual response, including vibrators and other types of massage-like movement devices and a suction device. One device described in U.S. Pat. No. 7,967,740 combines vibration, vacuum suction and oscillation to provide a combination of elements which are designed for treating female dysfunctions, such as sexual arousal disorders and female orgasmic disorders.

Women using devices such as that described in the '740 patent may also be working with a therapist or other healthcare professional in an effort to treat a particular disorder. Women may need to discuss the use of the device with the healthcare professional in order determine if the device is effectively treating the disorder and possibly change the settings on the device in order to improve the treatment. However, it may be difficult for women to describe their use of the device or relate changes in its operation to improvements in their sexual arousal.

Therefore, there is a current need for improving the ability of a patient and a healthcare professional to identify and understand the effectiveness of sexual stimulation devices in the treatment of female sexual disorders.

SUMMARY OF THE INVENTION

Embodiments described herein are directed to systems and methods for interactive treatments of female sexual disorders and/or to provide sexual enhancement, and more specifically to a programmable sexual stimulation device which transmits and receives data relating to the use and function of the device. The sexual stimulation device may be programmed to implement a particular combination of mechanical actions which have been customized by a user or a healthcare professional involved in the treatment of the user. The device may also collect data on the type of mechanical actions input by the user and transmit the data to a remote location for viewing by the user or the healthcare professional. The data from the device may be used to analyze the effectiveness of a particular treatment program and to determine future treatments with the device. The device may also communicate with external devices which aid in the treatment programs, such as audio or image display devices which can coordinate the function of the sexual stimulation device with the presentation of audio or visual information to provide additional sources of sexual arousal to the user.

From this description, in conjunction with other items, the advantages of the said invention will become clear and apparent more so based upon the hereinafter descriptions and claims, which are supported by drawings with numbers relating to parts, wherein are described in the following sections containing the relating numbers.

A sexual stimulation system is provided. The system includes a sexual stimulation device, a first computer in communication with the sexual stimulation device which receives usage data from the sexual stimulation device pertaining to the use of the sexual stimulation device by a user, and a remote computer which receives the usage data from the first computer, wherein a program is created on the remote computer for execution on the sexual stimulation device which is based upon the usage data.

A method of simultaneously treating a female sexual disorder and providing sexual stimulation is also described. The method includes creating a treatment program for execution on a sexual stimulation device, transmitting the treatment program to the sexual stimulation device for execution, receiving usage data from the sexual stimulation device, and modifying the treatment program based on the received usage data. Advantageously, the program is useful for promoting sexual response enhancement. Additionally or alternatively, the program may treat female sexual dysfunction. Optionally, the usage data is received by a health care provider. The health care provider can evaluate the usage data and modify the treatment program based upon the usage data.

The sexual stimulation device may include a suction element; a vibratory element; and an oscillatory element, which are independently operable and programmable. Preferably, these elements generate usage data. The usage data may be translated to a treatment protocol which controls one or more of the vibratory element, oscillatory element, and suction element.

In another aspect, a sexual stimulation apparatus is disclosed. The apparatus may include a plurality of elements which provide a stimulus to a female genital area, a controller unit which controls the execution of the elements, a memory unit which stores usage data relating to the execution of the elements; and a communication unit which transmits and receives data relating to the use of the plurality of elements to a remote device.

Optionally, the sexual stimulation apparatus further measures a user's physiological response to use of the device, and stored data indicative of the response in the memory. Advantageously, the operation of the sexual stimulation apparatus is based at least in part on the measurements of physiological response. Physiological response may be measured based upon clitoral tumescence, vaginal lubrication, orgasmic intensity etc. or a combination thereof.

In another aspect, the usage data allows a user to program or re-program the device based on user preference. In still another aspect, the usage data allows a user to program or re-program the device based on treatment goals or results. The usage data may allow a user to program or re-program the device based on a combination of user preference and treatment goals or results.

Furthermore, a sexual stimulation apparatus for enhancing female sexual response is provided. The apparatus may include a housing unit; a vibratory element; an oscillatory element; and a removably attached suction element; wherein the suction element includes a flexible portion having as a first position where the suction element can be retracted and substantially flush with the housing unit and a second position, where the suction element is configured to be extended for contact with a user's skin surface. Optionally, the suction element can be removed and replaced with an alternative actuator such as a heating element, a lubricant dispenser, a medicament dispenser, or a finger-shaped tip configured for sexual stimulation and enhancement.

In another aspect, a multi-functional device for sexual stimulation is disclosed. The device includes a housing unit having a top portion and a bottom portion. The top portion is constructed from a substantially rigid plastic. The bottom portion may be constructed from a substantially flexible, biocompatible material. The device may further include a vibratory element, an oscillatory element, and a suction element, wherein the elements are housed in a housing unit. Preferably, the substantially flexible, biocompatible material is silicone or latex. Optionally, the flexible material is impregnated with a fragrance. Additionally or alternatively, the bottom portion may have a texture for improving grip and promoting pleasure. The bottom portion may include a heating element. The oscillatory element may include massage thumbs supported by balls or a plurality of rollers.

BRIEF DESCRIPTION OF THE DRAWINGS

The accompanying drawings, which are incorporated in and constitute a part of the specification, illustrate embodiments of the invention and, together with the description, serve to explain the objects, advantages, and principles of the invention. In the drawings:

FIG. 5D is a cross sectional view of an actuator attached to the port of the suction element in one embodiment of the invention.

DETAILED DESCRIPTION OF THE PREFERRED EMBODIMENT

Figure 1:
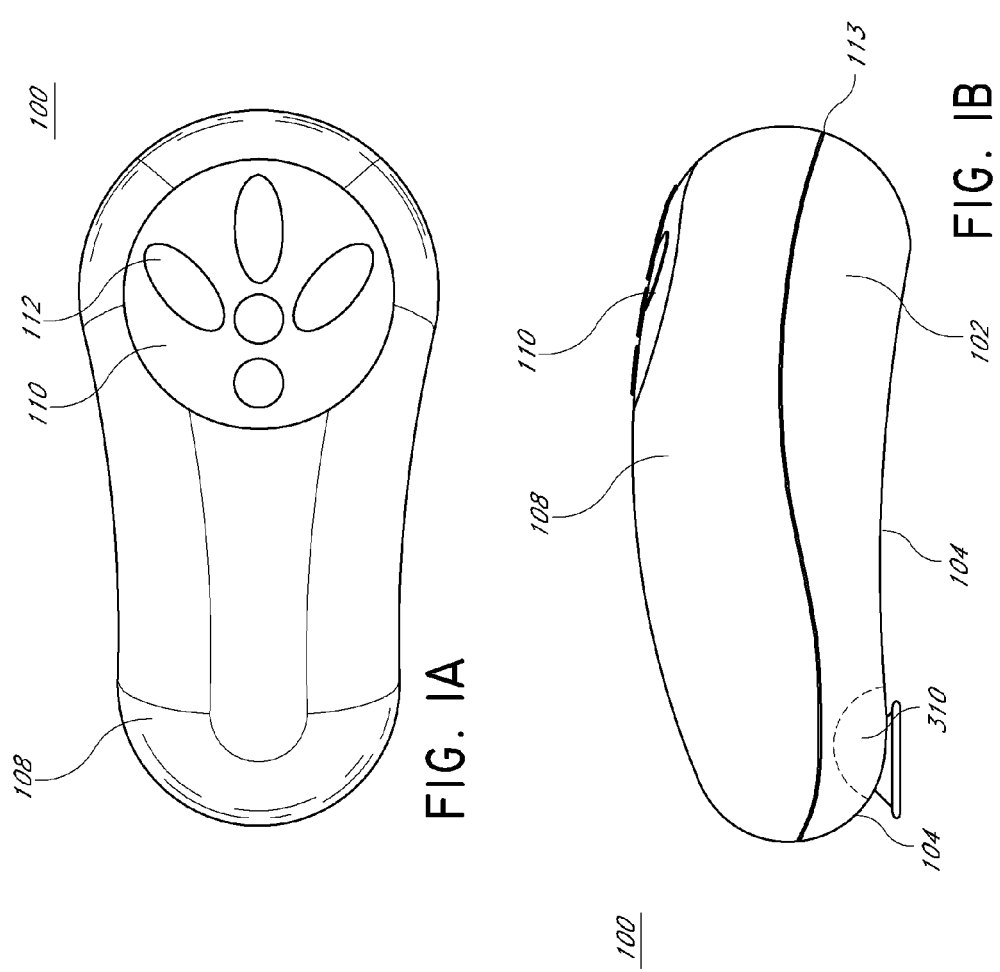
FIGS. 1A and 1B are illustrations of a sexual stimulation device useful for treating a female sexual disorder, according to one embodiment of the invention.

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

Sexual drive is one of the most fundamental drives that humans experience yet can often be frustrated. The present invention provides a sexual stimulation device and method for the treatment of female sexual dysfunction and promotion of sexual enjoyment and pleasure. More particularly, the device and methods described herein address, among other conditions, females who have difficulty achieving orgasm. According to the DSM-IV-TR, the Diagnostic Manual of Mental Disorders, 4$^{th}$ Edition, "female sexual dysfunction" refers to any number of sexual disorders. As used herein, the phrase "female sexual dysfunction" includes, without limitation sexual desire disorders such as hypoactive sexual desire disorder and sexual aversion disorder, sexual arousal disorders such as female sexual arousal disorders, as well as orgasmic disorders such as female orgasmic disorders and sexual pain disorders. Also included within the meaning of "female sexual dysfunction" are sexual dysfunction disorders due to a general medical condition. In certain embodiments, a device for the treatment of urinary incontinence is provided. As used herein, "sexual stimulation device" is meant to include a medical device for treating sexual dysfunction and/or urinary incontinence as well as a device for personal, non-medical use to enhance pleasure. More particularly, the device as described herein can be medically indicated for use with the external female genitalia to treat sexual dysfunction, improve orgasmic potential, and reduce the symptoms of urinary incontinence. Additionally, the device can be used in a non-medical capacity to enhance the user's sexual function and enjoyment. While many sexual arousal and stimulation devices have been developed, this invention is based in part on the discovery and development of a sexual stimulation device which enhances sexual function, promotes urogenital function, and increases orgasmic potential with use over time, both as a medical device and a device for pleasure.

The female genitalia, as used herein, describe the external female genital organs, also known as the vulva. The vulva includes the labia majora, labia minora, the vestibule of the vagina, and the clitoris. The clitoris, a highly sensitive sex organ which, when stimulated appropriately, provides sexual satisfaction. A small cylindrical organ, the clitoris is located at the anterior part of the vulva. During sexual intercourse, the penis is reciprocally and slidingly received in the vagina. However, the penis typically does not make significant contact with the clitoris but rather, the abdomen and the transition area from which the base of the penis extends provides the critical contact that may ultimately lead to orgasm. Sexual satisfaction in females generally is not derived from linear translation of the penis through the vagina, but rather by rhythmic pressure against and/or frictional engagement with the clitoris.

Urinary incontinence, as used herein, includes, without limitation, stress incontinence, urge incontinence, functional incontinence and other types of incontinence including overflow incontinence. In certain aspects of the invention, a device and method for treating symptoms of urinary incontinence is provided. Symptoms include, without limitation, overactive bladder symptoms, the unintentional loss of urine, inability to hold urine in the bladder due to loss of voluntary control over the urinary sphincters resulting in the involuntary passage of urine, and the involuntary contract of the muscular wall of the bladder resulting in urinary urgency, an immediate unstoppable need to urinate. While the invention is described predominately in the context of a device for treating sexual dysfunction and for promoting sexual stimulation, it is equally well-suited for treating urinary incontinence. As described in U.S. Pat. No. 7,967,740, the application of direct suction on the clitoral head by the suction element, for example, stimulates the surrounding clitoral tissue and promotes the directed aggregation of blood flow to the surrounding tissues. This, in turn, only optimizes orgasmic potential. The use of the device can encourage contraction and thus strengthening, of the vaginal and pelvic floor muscles such that the contraction can improve symptoms of female urinary incontinence.

Sexual Stimulation Device

One embodiment of the invention provides a sexual stimulation device 100, as illustrated in FIGS. 1A and 1B. FIG. 1A primarily illustrates a bottom surface 102 of the sexual stimulation device 100, which includes an interaction area 104 designed to interact with female sexual anatomy, and particularly the clitoris. FIG. 1B primarily illustrates a bottom surface 102, from a side perspective, of the sexual stimulation device 100. The sexual stimulation device 100 is enclosed by a housing 106 which is shaped to ergonomically fit the female genital region.

A top surface 108 of the sexual stimulation device 100, illustrated in FIG. 1B, includes one or more interactive controls 110 which the user can interact with to change the behavior of the sexual stimulation device 100. In one embodiment, the device is configured with a plurality of different types of action, including vibration, oscillation and vacuum suction, as disclosed in U.S. Pat. No. 7,967,740, the contents of which are incorporated by reference herein in their entirety. This multi-modal operation includes advantageously three sets of physical stimuli applied to the genitals of a female patient for the purpose of enhancing sexual arousal. The controls 110 can have simple bi-directional up and down buttons that adjust the speed and rhythm of the oscillation, the intensity of the vibration and the power and speed of pulsation of the vacuum pressure. It will be appreciated, however, that the controls can be incorporated into a capacitive membrane/control keypad. Each function operates independently of the other, and provides for controls to turn off any of the functions while the others continue to operate. In one embodiment, the control panel is configured to glow in the dark. While not illustrated in FIG. 1, the sexual stimulation device 100 may likewise or alternatively include a lighting element for illuminating the device 100. Suitable lighting elements include, for example, a light-emitting diode (LED) light. The LED or LEDs can be selected from any combination of single color, multiple color, multiple piece, standard, and special LED assemblies which are commercially available.

The vibration refers to the application of a relatively high frequency of vibration speed of approximately 10 Hz-200 Hz. Vibration can be axial, radial and/or rotational. Alternatively or additionally, frequencies can be in the range 0.5-400 Hz and/or amplitudes in the range 0.1 micron to 500 micron. Alternatively or additionally, various motion wave forms may be used, for example square waves, saw-tooth waves and/or sine-waves. As will be described in greater detail below, the vibration feature is adjustable and programmable. For example, any intermediate value of vibration parameters can be applied as well as well as more extreme values.

The oscillation movement provides for a relatively slow speed of between about 0.5 Hz-5 Hz, and provides a linear massaging motion on each side of the vaginal opening as will be described in greater detail below with reference to FIGS. 3A-3C, 4, and 6A-8.

The interactive controls 110 permit the user to adjust the levels of these various actions in order to increase, decrease, stop or start the vibration, oscillation and suction. The interactive controls also allow the user to select programs which run a predetermined sequence of actions on the device, as will be described further herein. The interactive controls 110 can include one or more buttons 112, such as those in FIG. 1B, or other types of interactive controls, such as a touchpad, touchscreen, capacitive or thermal sensors.

The housing 106 of the sexual stimulation device 100 is preferably water resistant and more preferably waterproof in order to protect the internal components from exposure to liquids which may contact the exterior surface of the sexual stimulation device 100, such as lubricants or bodily fluids produced by the female during use of the device. The surface of the housing 106, and specifically the bottom surface 102, can also be selected to create a specific tactile feel. The surface material is selected to create a certain level of friction, which then translates to heat, or which has a specific texture that increases arousal. Optionally, the sexual stimulation device 100 can contain a reservoir of lubricant 110 (see FIG. 3) which is excreted at the interaction area 104 in order to improve the comfort while using the device. Pumped lubricant can be dispensed from the reservoir by, for example, pressing on a small button actuator to move a valve diaphragm (not shown). Alternatively, the dispensing of lubricant can be programmed to dispense according to user's preferences or medical requirements. The lubricant can be applied to the exposed skin to moisten the vulva for reduction of friction and to promote a pleasurable effect.

The top surface 108 of the housing 106 is substantially rigid in construction. Suitable construction materials can include a rigid, molded plastic, for example. The bottom surface 102 of the housing 106 is preferably constructed from a substantially flexible, biocompatible material such as a silicone or medical grade, non-allergenic latex or other suitable materials and specific embodiments of the bottom surface 102 will be described with reference to FIGS. 13A-13D. The top surface 108 and bottom surface 102 are fused together at interface 113.

Figure 13A:
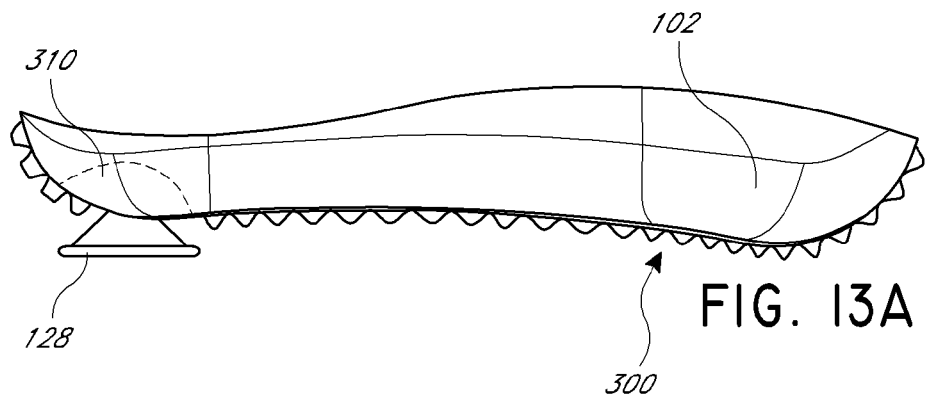
FIG. 13A-13D are side views of various embodiments of the bottom portion of the sexual arousal device.
Figure 13B:
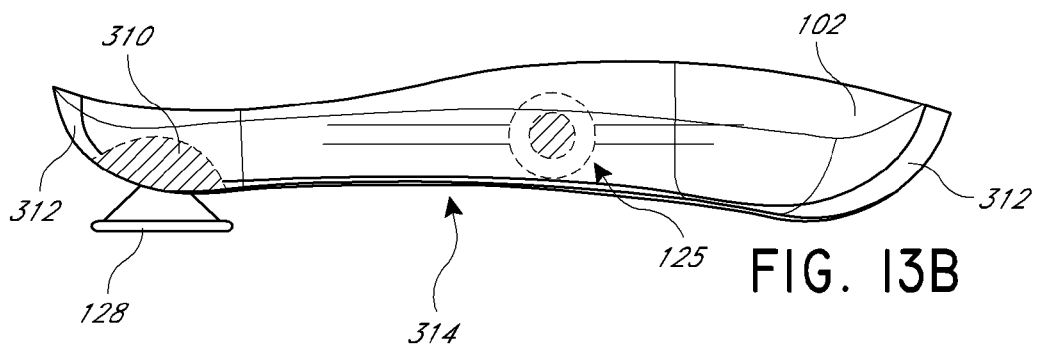
Figure 13C:
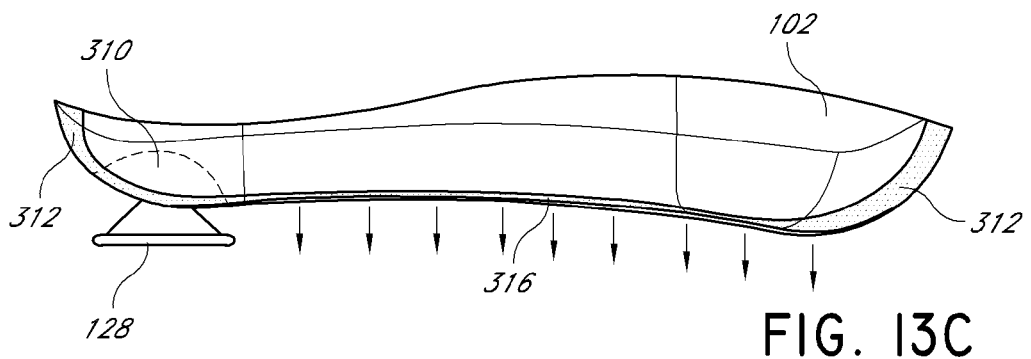
Figure 13D:
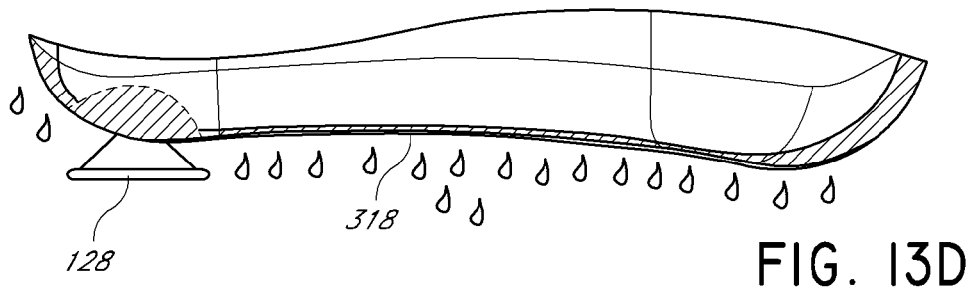

FIGS. 13A-13D are side views of some examples of the bottom surface 102 of the device. Turning to FIGS. 13A-13D, the bottom surface 102 is configured to fit snuggly to the device and allow the oscillatory elements (as will be described in greater detail below) to provide close contact with the user's skin. FIG. 13A illustrates a side view of the bottom surface 102 of the device. The bottom surface 102 is constructed from a soft, rubber-like material. As illustrated, the material includes bumps 300 or other surface treatments to enhance the user's sexual arousal. A cavity 310 is created whereby the suction element 128 can extend through the bottom surface 102 to contact the user's skin as will be described in greater detail with reference to FIGS. 5A-5C. The material can further include colors, scents, or other features which would further enhance the user's pleasure as will be described with reference to FIGS. 13B-13D. FIG. 13B illustrates an alternative embodiment, wherein the bottom portion 102 of the device is constructed from a flexible, biocompatible material having relatively thicker end portions 312 and a thinner middle portion 314. The varied thick/thin profile allows for the device to conform more accurately to the user's anatomy. The thicker portions 312 connect to the upper housing portion 108 and around the suction cup cavity 310. The thinner portion 314 allows for the oscillatory element 125 to come into close contact with the user's skin surface and conform with the topography of the user's skin surface, and the user's clitoral glans in particular, more readily, thereby enhancing the user's sensation and pleasure. With reference to FIG. 13C, the bottom portion 102 of the housing unit can include a layer 316 of treated biocompatible material such as silicone or latex which has been impregnated with a fragrance. In FIG. 13D, the bottom portion 102 can include a layer 318 of flexible biocompatible material which is at least partially porous such that an oil or other lubricant can be released from the inside of the device through the semi-porous layer 318. In another embodiment, the housing can include a removable sleeve (not shown) which is configured to fit over the bottom portion 102 of the device. The removable sleeve is likewise constructed from a biocompatible, flexible material such as silicone such that the sleeve provides a soft cover over at least the bottom portion of the housing. In one aspect, the removable sleeve is disposable. Optionally, the sleeve can be fitted with a thermal element for warming the device 100. In another aspect, the sleeve includes patterning such as molded bumps or ridges to reinforce the rolling action of the device, improve the grip, and provide for embellishment of the housing. Other features can include, without limitation, a releasable fragrance, a bioeffecting or body-treating material, and/or a glow-in-the dark element.

Figure 2:
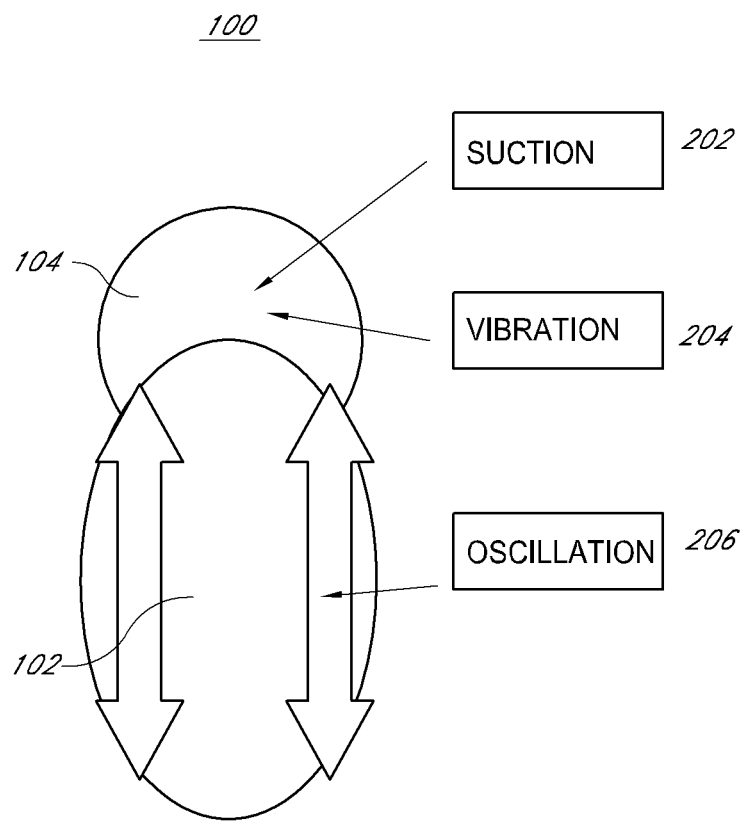
FIG. 2 is a schematic illustration of the sexual stimulation device illustrating the areas of movement of the device, according to one embodiment of the invention.

FIG. 2 is a schematic illustration of the sexual device 100 and illustrates the areas of movement of the sexual stimulation device 100, according to one embodiment of the invention. The suction movement 202 and vibration movement 204 are located at the interaction area 104 of the device 100, while the oscillation movement 206 is located on the bottom surface 102 of the device 100.

Figure 3A:
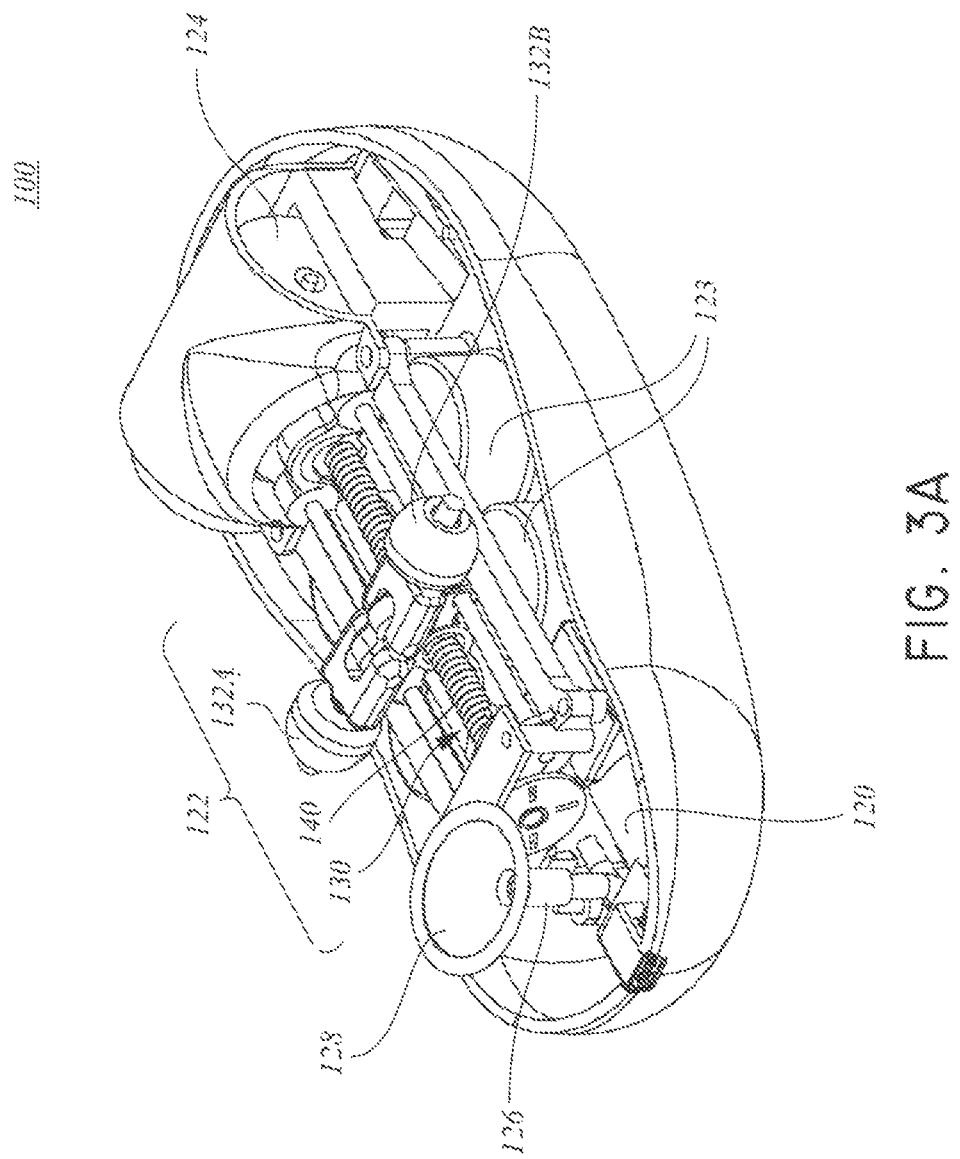
FIG. 3A is a three-dimensional view of the sexual stimulation device with the bottom portion of the housing removed.
Figure 3B:
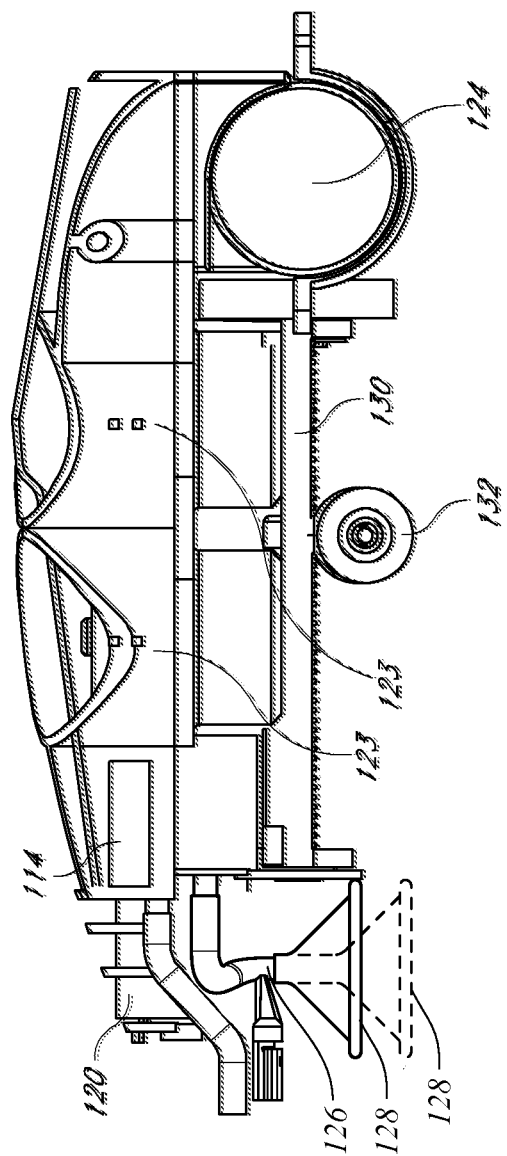
FIG. 3B is a side plan view of the internal components of the sexual arousal device according to one embodiment of the invention.
Figure 3C:
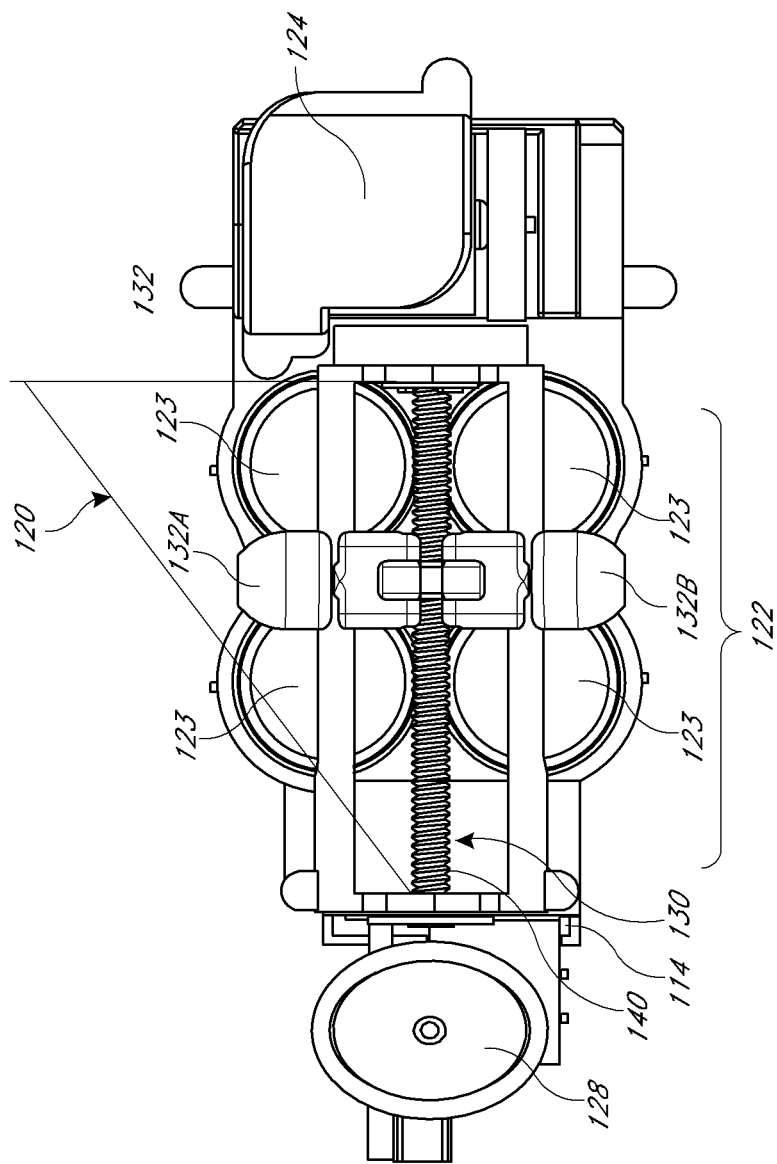
FIG. 3C is a bottom plan view of the internal components of the sexual arousal device according to one embodiment of the invention.

FIGS. 3A, 3B, and 3C illustrate one embodiment of the internal components of the sexual stimulation device 100. FIG. 3A is a three-dimensional view of the sexual arousal device illustrating the sexual arousal with the bottom portion of the housing removed. Turning to FIG. 3B, the device 100 is preferably electrically operated by a battery 114. It will be appreciated, however, that the device can be operated with one or more 1.5 volt batteries, A/C operation or operation by other battery configurations is also contemplated as is powering via a USB connection, as will be described in greater detail below. Though not illustrated in FIG. 3B, the device 100 can include a lubricant reservoir and lubricant pump. Preferably, the device includes a vacuum pump 120 and longitudinal movement mechanism 122 as seen in FIG. 3C. The sexual stimulation device 100 can also include a vibration motor 123 or plurality of motors separate from the motor 124 which powers the longitudinal movement mechanism 122. The vibration motor 123 could be a pulsating motor or a piezoelectric motor which creates a sonic-type vibration. The vibration motor 123 can have an eccentric weight mounted to its shaft, which applies overall vibration to the entire device. The weight is preferably about 100 mm H 4 mm circular weight, 500-10000 RPM. In an alternate embodiment, an acoustic wave generated at the interaction area creates the desired vibration. Notably, vibratory stimulation has therapeutic and beneficial effects on human body tissue. Vibration at low frequencies applied to tissue increases blood circulation due to the increase in capillary dilation and the increased blood flow increases the consumption of oxygen and nutrients by muscles. This, in turn, results in improvement of collagen regeneration, improved muscle tone, elasticity, and contractile capacity.

The vacuum pump 120 is attached with a tubing 126 which extends from the vacuum pump 120 to the interaction area 104 in order to provide a suction effect at the interaction area 104. The function and benefits of the vacuum suction are described in the '740 patent and are not separately repeated herein, although the vacuum pump is generally a 30 mA operating at 12V. In one embodiment, the device is equipped with a suction element 128 (see FIG. 1A and FIGS. 5A-5D) removably connected with the outer end of the tubing 126 in order to create a seal around an area of the clitoris and effectuate the suction force on the outer surface of the clitoris. The vacuum pump 120 applies suction to the clitoris directly and he operates with a variable negative pressure. The suction element 128 is further illustrated in FIGS. 5A-5D.

Oscillation is provided comprising a first massage thumb 132A and second massage thumb 132B. The massage thumbs are powered by the motor 124 and can be programmed for independent movement of the massage thumbs 132A, 132B. This independent movement may allow one of the massage thumbs to move in one direction while another massage thumb moves in the opposite direction, providing a unique sensation for the female user. The gear motor can be a 16 mm brushed motor operating at 160 mA at 12V, although they can be run at 9V or custom wound for 9V. Other small motors could be used. Alternatively, the gear motor comprises a worm-drive, friction drive, a crown/face gear system, or bevel gears. In operation, the thumbs move in conjunction, applying pressure to the labia. The speed, patterning, direction, and intensity of the massage thumbs 132A, 132B are adjustable and programmable.

Figure 4:
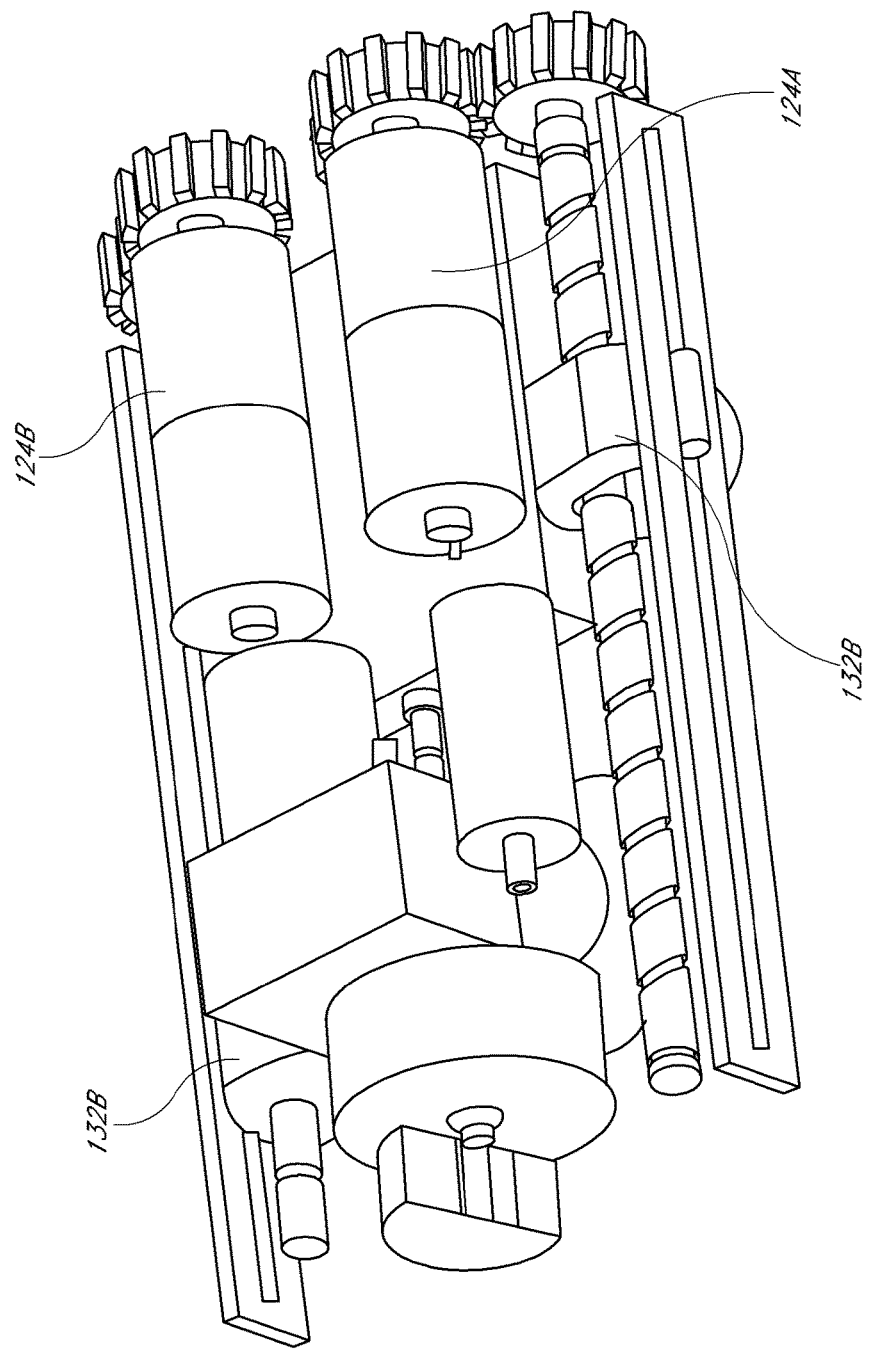
FIG. 4 is a perspective view illustration of an alternate embodiment of the internal components of the sexual stimulation device, according to one embodiment of the invention.

FIG. 4 illustrates an alternate embodiment of the internal components of the sexual stimulation device, according to one embodiment of the invention. With reference to FIG. 4, in one embodiment shown in FIG. 4, an oscillatory element 125 is provided comprising a first gear motor 124A and a second gear motor 124B to provide separate movement to a first massage thumb 132A and second massage thumb 132B, thus providing for independent movement of the massage thumbs. This independent movement would allow one of the massage thumbs to move in one direction while another massage thumb moves in the opposite direction, providing a unique sensation for the female user. The gear motor can be a 16 mm brushed motor operating at 160 mA at 12V, although they can be run at 9V or custom wound for 9V. Other small motors could be used. Alternatively, the gear motor comprises a worm-drive, friction drive, a crown/face gear system, or bevel gears. In operation, the thumbs move in conjunction up and down the vaginal cleft, applying pressure to the labia and clitoral crura. The variable speed motors 124 are reversible and their motion patterns are programmable.

The longitudinal movement mechanism 122 can include the gear motor 124, lead screw 130, massage thumbs 132 and longitudinal tracks 134 on which the massage thumbs 132 move. The gear motor 124 drives the lead screw through a series of connected gears 136, causing the lead screw 130 to turn in a clockwise or counterclockwise motion. A central support structure 138 is connected with the lead screw 130 and moves up and down the length of the lead screw 130 along a spiral-shaped track 140 formed in the lead screw. In one embodiment, the lead screw is configured for between about 0.25-0.35" per revolution. The central support structure 138 is connected with the massage thumbs 132 via lateral support rods 142 which extend from the central support structure 138 perpendicularly from the lead screw 130. The massage thumbs 132 are movingly connected with the longitudinal tracks 134 to provide support for their movement, and the massage thumbs 132 protrude into or through the bottom surface of the housing to translate the movement to the outside of the sexual arousal device. The oscillatory element is further illustrated in FIGS. 6A, 6B, 7, and 8 and described in greater detail with reference to these figures.

Figure 5A:
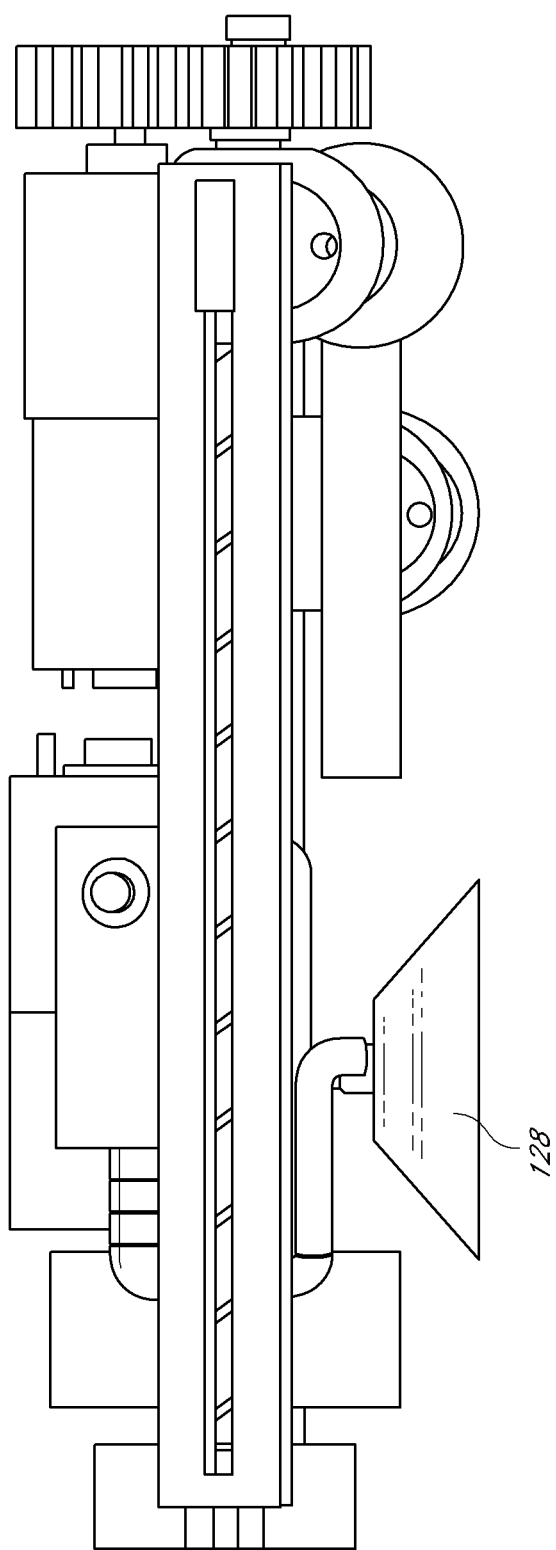
FIG. 5A is a side view illustration of the internal components of the sexual stimulation device, according to one embodiment of the invention.

FIG. 5A is a side view illustration of the internal components of the sexual stimulation device 100, according to one embodiment of the invention. FIG. 5 particularly illustrates the suction cup 128 located at the interaction area 104 of the device 100 (see FIG. 1A). The suction movement can be applied by a small air vacuum pump being applied directly to the clitoral glans by forming a vacuum seal at the labial commissure. The suction cup 128 is configured to be adjustable so that it can be extended outward and away from the housing to protrude further to optionally accommodate the clitoris. In a preferred embodiment, the suction cup 128 is formed from a biocompatible matter that is optionally disposable.

Figure 5B:
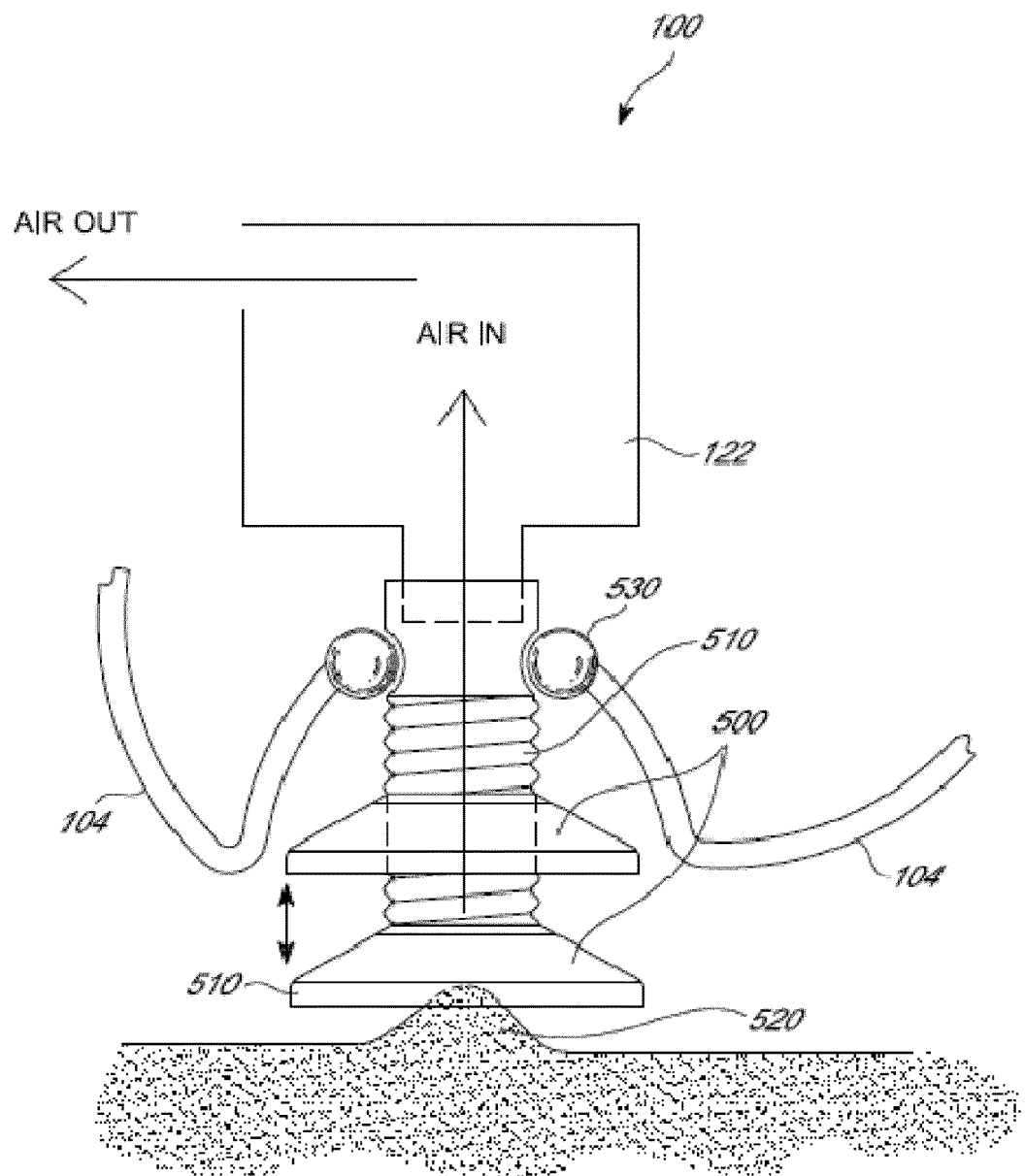
FIG. 5B is a cross sectional view of one embodiment of the suction element of the sexual stimulation device.

FIG. 5B shows a cross sectional view of the interaction area 104 of the device 100. The suction element 128 comprises a substantially frusto-conical portion 500 constructed of a relatively soft and flexible biocompatible material for contact with the user's skin surface 520. The frusto-conical portion 500 is attached to a flexible gooseneck tubing 510 with accordion like movement that can be extended downward to contact the clitoral glans of the user or retracted upward to become flush with the device. FIG. 5B illustrates the suction element 128 both in the retracted state where it is flush with the device and in the extended position, wherein the suction element is in contact with the user's skin surface 510. The gooseneck tubing 510 is attached to the vacuum pump 122 with a seal 530. In one embodiment, the seal 530 is an O-ring.

In one aspect of the invention, the suction cup 128 further comprises a filter (not shown) at the juncture between the cup 128 and the gooseneck tubing 510 as the gooseneck tubing 510 is likely to pull in foreign materials such as lubricants or secreted bodily fluids during operation.

Figure 5C:
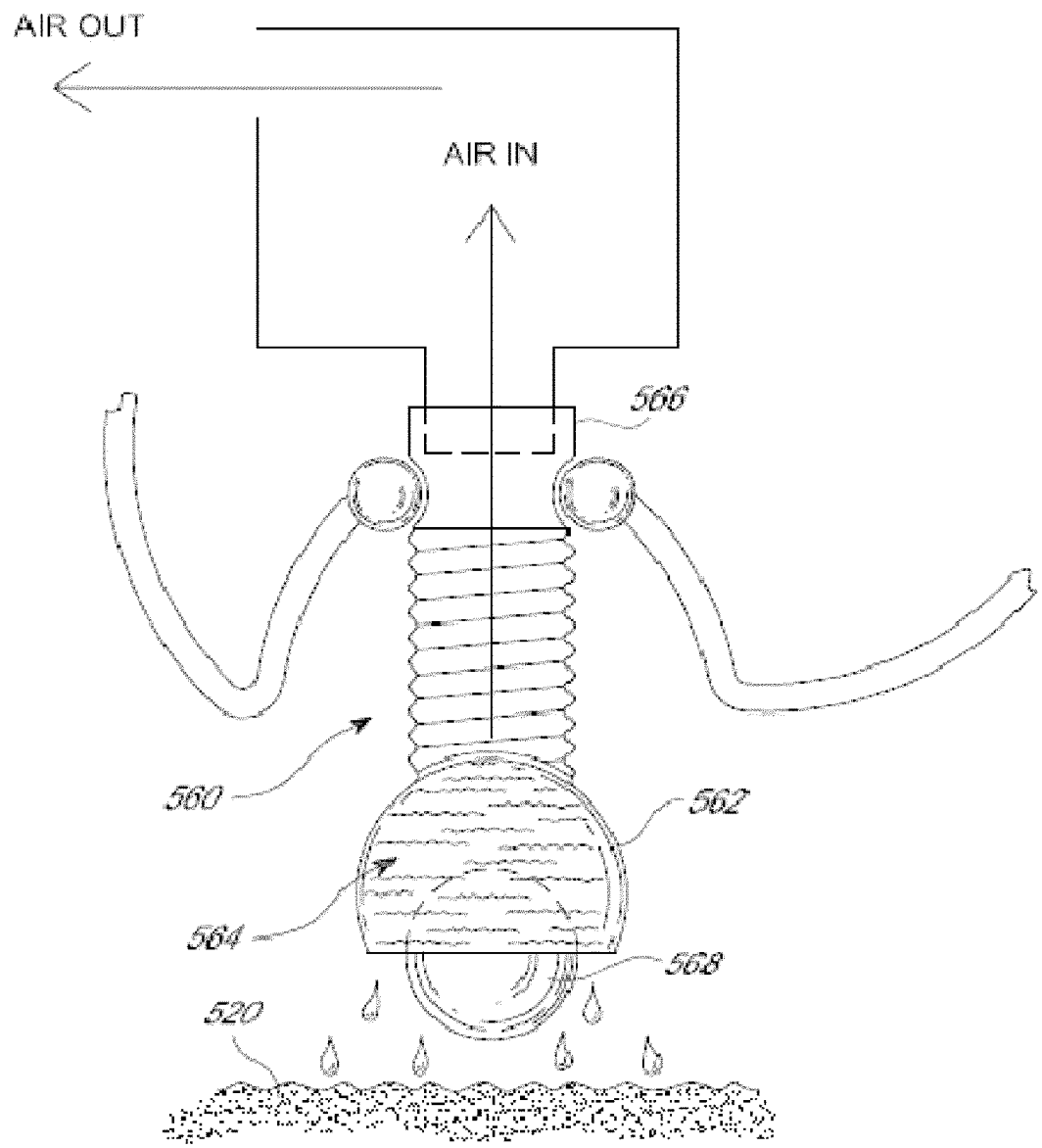
FIG. 5C is a cross sectional view of an actuator attached to the port of the suction element in one embodiment of the invention.

In one embodiment, the interaction area 104 includes an interchangeable port (not shown) for a user to remove and attach different types of mechanical actuators. For example, the suction cup could be removed and replaced with an oscillator attachment, such as the oscillatory disc described in the '740 patent. FIGS. 5C and 5D illustrate alternative actuators which can be removably attached to the device 100 at the interchangeable port. In FIG. 5C, the actuator 560 comprises a dispenser 562 housing a liquid 564. The actuator 560 is connected to the device 100 at an interchangeable port once the suction cup has been removed. The dispenser 562 includes a liquid 564 stored within said dispenser 562. The liquid 564 can include a lubricant such as water-based personal lubricants, oil-based personal lubricants, organic or natural lubricants, and silicone based lubricants. In another embodiment, the dispenser 562 is adapted for applying a topical medication to the user in proximity of the user's skin surface 520. The liquid 564 can be a medicament. The medicament can be useful in the treatment of female sexual dysfunction and can include, without limitation any one or combination of the following medicaments: Androsorb™ testosterone cream, Alista™ prostaglandin, Estrace™ estrogen cream, Evista™ estrogen, Femprox™ vasodilator, Premarin™ estrogen cream, Steryl-Norleucine VIP cream, testosterone creams, and testosterone gels. A sphere 568 is disposed at the bottom of the dispenser 562 and provides for a liquid 564 to be rolled onto the surface of the user's skin 520. In another embodiment, as illustrated in FIG. 5D, the sexual stimulation device 100 optionally includes any number of removable actuators 601, 602, and 604. With reference to FIG. 5D, the gooseneck tubing 510 is adapted to receive an actuator 600 to enhance the sexual arousal and sexual satisfaction of the user. Actuator 600 can be removed and replaced with actuators 601, 602, or 604, for example. Actuator 601 includes a heating element 608 at the bottom surface of the actuator 601 for warming the user skin 520 at the site of interaction. Actuator 601 can be removed and replaced with actuator 602 or actuator 604. As illustrated, actuator 602 is configured to assume the shape of a finger. The actuator 602 includes a flexible portion 603 to allow the upper portion of the finger to flex. Actuator 604 includes at least one ball 610 which can be rolled over the surface of the user's skin 520 for further stimulation.

Figure 6A:
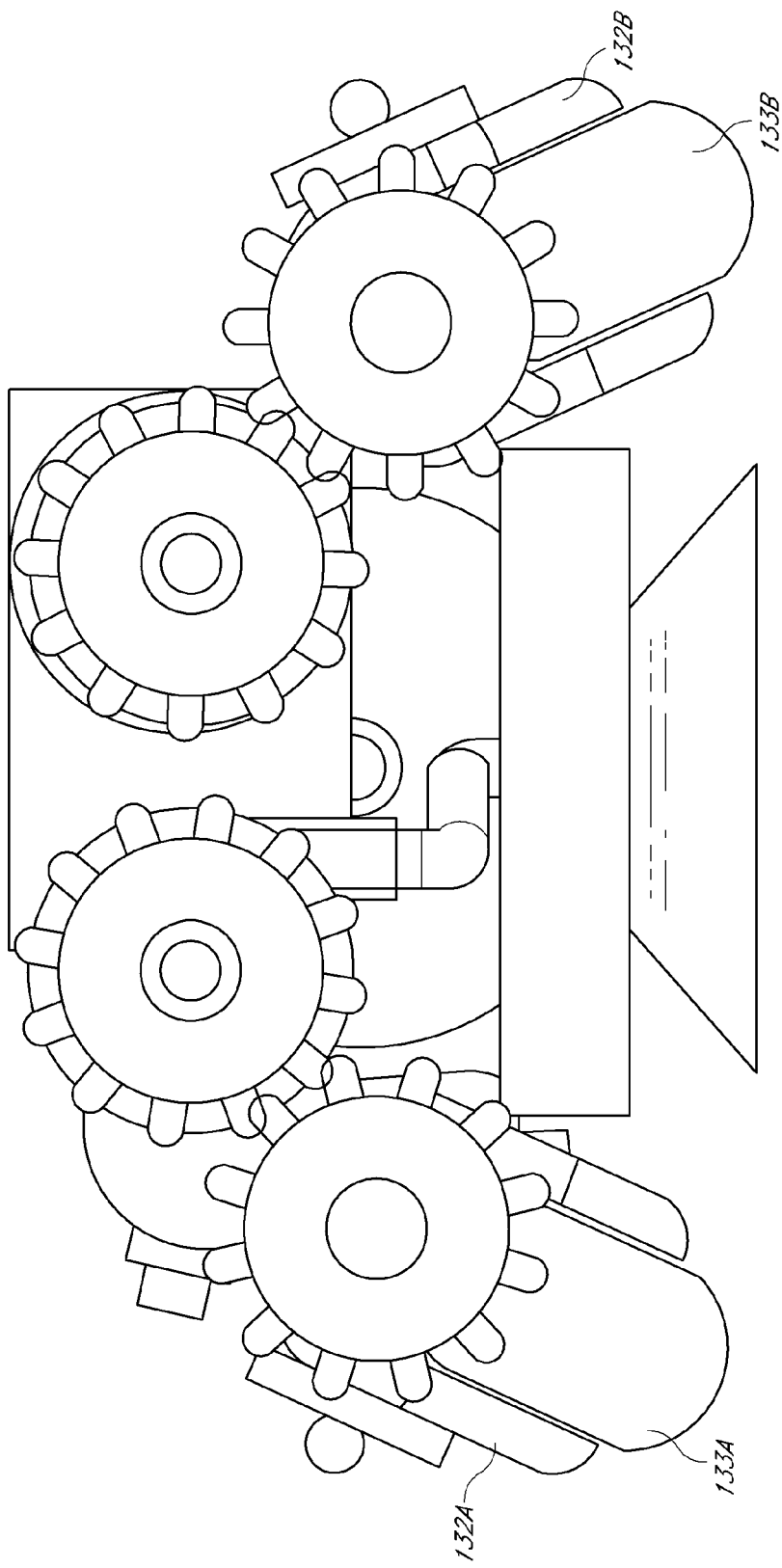
FIG. 6A is a cross-sectional view illustration of the internal components of the sexual stimulation device in an open-angled wheel configuration, according to one embodiment of the invention.
Figure 6B:
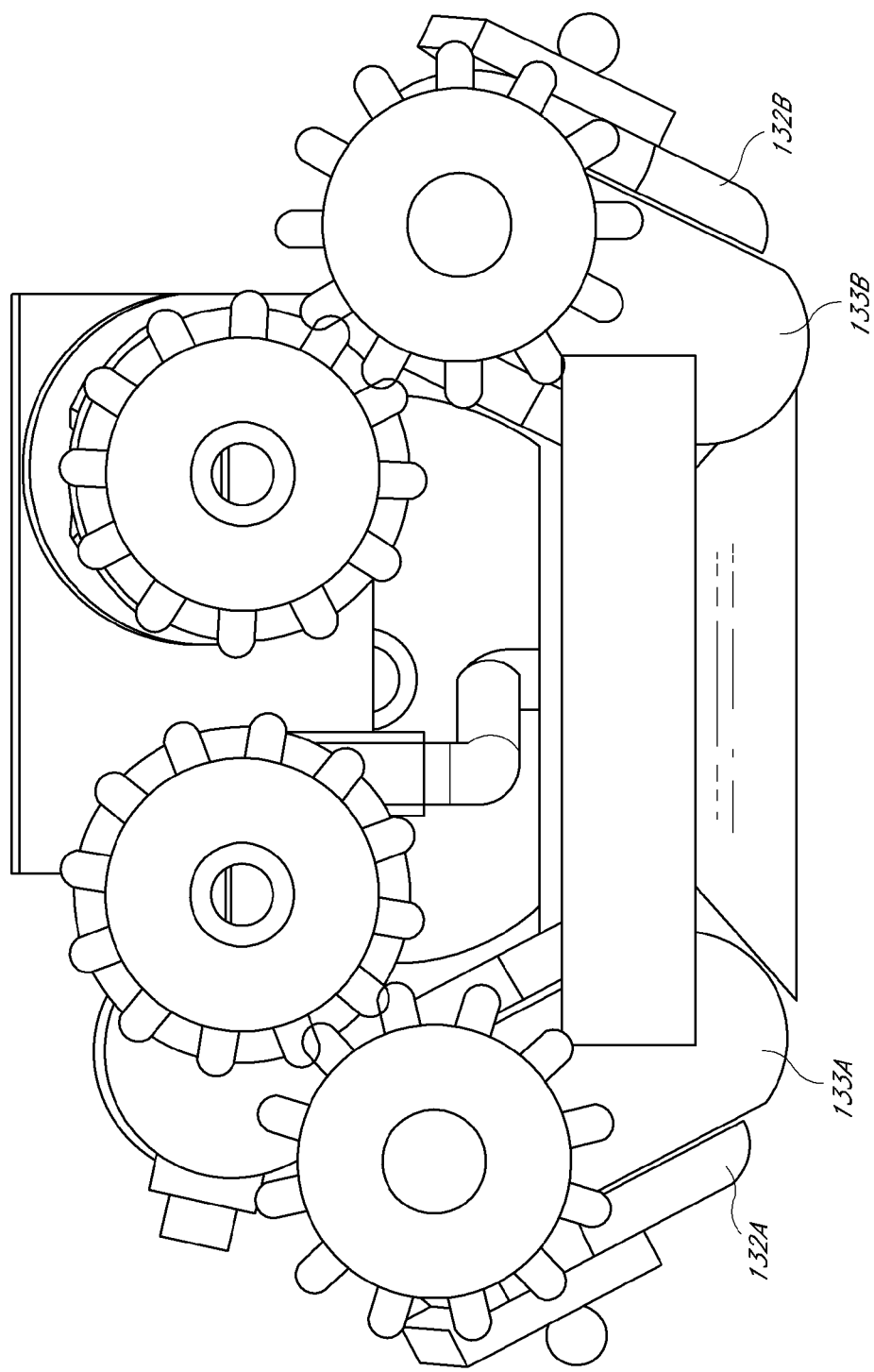
FIG. 6B is a right-side view illustration of the internal components of the sexual stimulation device in a closed-angled wheel configuration, according to one embodiment of the invention.

FIG. 6A is a cross-sectional view illustration of the internal components of the sexual stimulation device, illustrating a first wheel 133A and a second wheel 133B protruding from the respective first massage thumb 132A and second massage thumb 132B to provide for better movement along the bottom surface of the device 100. In the embodiment illustrated in FIG. 6A, the wheels 132A and 132B are set in an open-angled wheel configuration with the wheels angled toward the outer edges of the device 100, according to one embodiment of the invention. FIG. 6B is an alternate embodiment showing a closed-angled wheel configuration with the wheels angled inward toward a center of the device. The device may be configured to alternate between the open-angled and closed-angled configurations to provide for additional options that may be desirable to the user.

Figure 7:
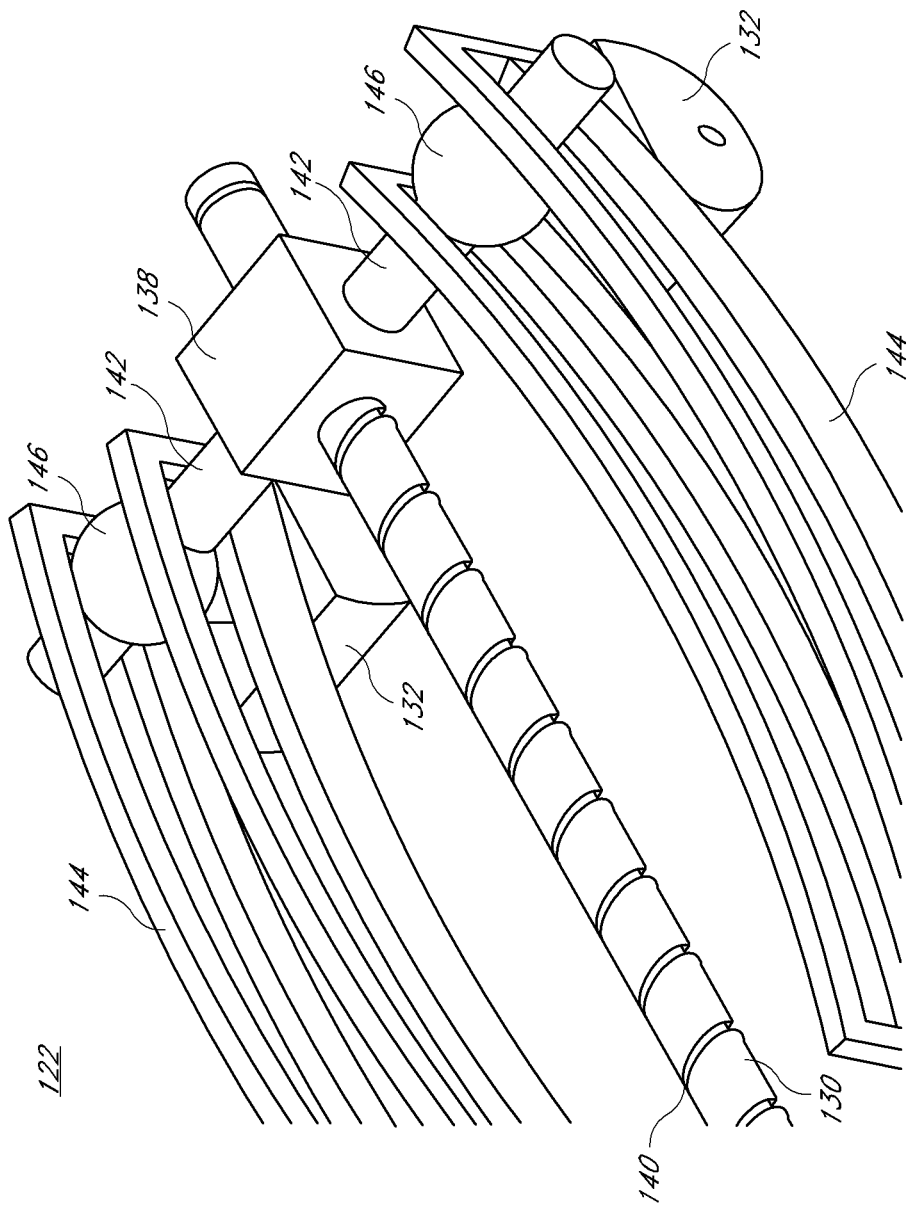
FIG. 7 is an illustration of an independent movement device disposed within the sexual stimulation device, according to one embodiment of the invention.

An alternate embodiment of a longitudinal movement mechanism 122 which provides movement along the bottom surface of the sexual stimulation device is shown in FIG. 7. The movement mechanism described herein provides for longitudinal movement of the massage thumbs (the oscillation feature) along tracks 144 on either side of the actuator 130. The tracks 144 are positioned parallel to the bottom surface of the sexual stimulation device such that the massage thumbs 132 protrude into or through the housing to translate the movement to the outside of the sexual stimulation device. The massage thumbs 132 are supported by rollers 146. In certain embodiments, the rollers 146 can be replaced with balls which are loosely fitted over the lateral support rods 142. A motor (not shown), such as a small brushless motor, is connected with one end of the actuator 130 and actuates the actuator in a clockwise or counterclockwise motion, which causes the central support structure 138 to move up and down the length of the actuator 130 along the spiral-shaped track 140 formed in the actuator 130. As the central support structure 138 moves along the actuator 130, the lateral support rods 142 move as well, causing the rollers or balls 146 to slide laterally along the lateral support rods 142 as the tracks 144 extend outward from the central support structure 138 and then move back inward on the peripheral ends of the tracks 144. The attached massage thumbs 132 therefore move along the bottom surface of the sexual stimulation device in a unique curved movement that provides a desired sensation to the female user.

Oscillation may be applied by two independently-positionable actuators, or probes, which are pressure-points that align on each side of the vagina over the labia majora and labia minora. These pressure points may also be referred to as thumbs, probes or styli. The thumbs can be programmable to move independently, applying pressure up and down the labia. The motors are reversible and variable speed for independent control of stimulation of each side of the vagina. In addition, the probes are mounted on axles which allow them to roll as they ride against a flexible membrane that applies the moving pressure-points to the patient's vulva. Friction and direct loads to the motor drive can be minimized with this configuration. In one embodiment, the linear travel of the thumbs would be approximately 3 inches at a maximum rate of approximately 12 inches per second.

Figure 8:
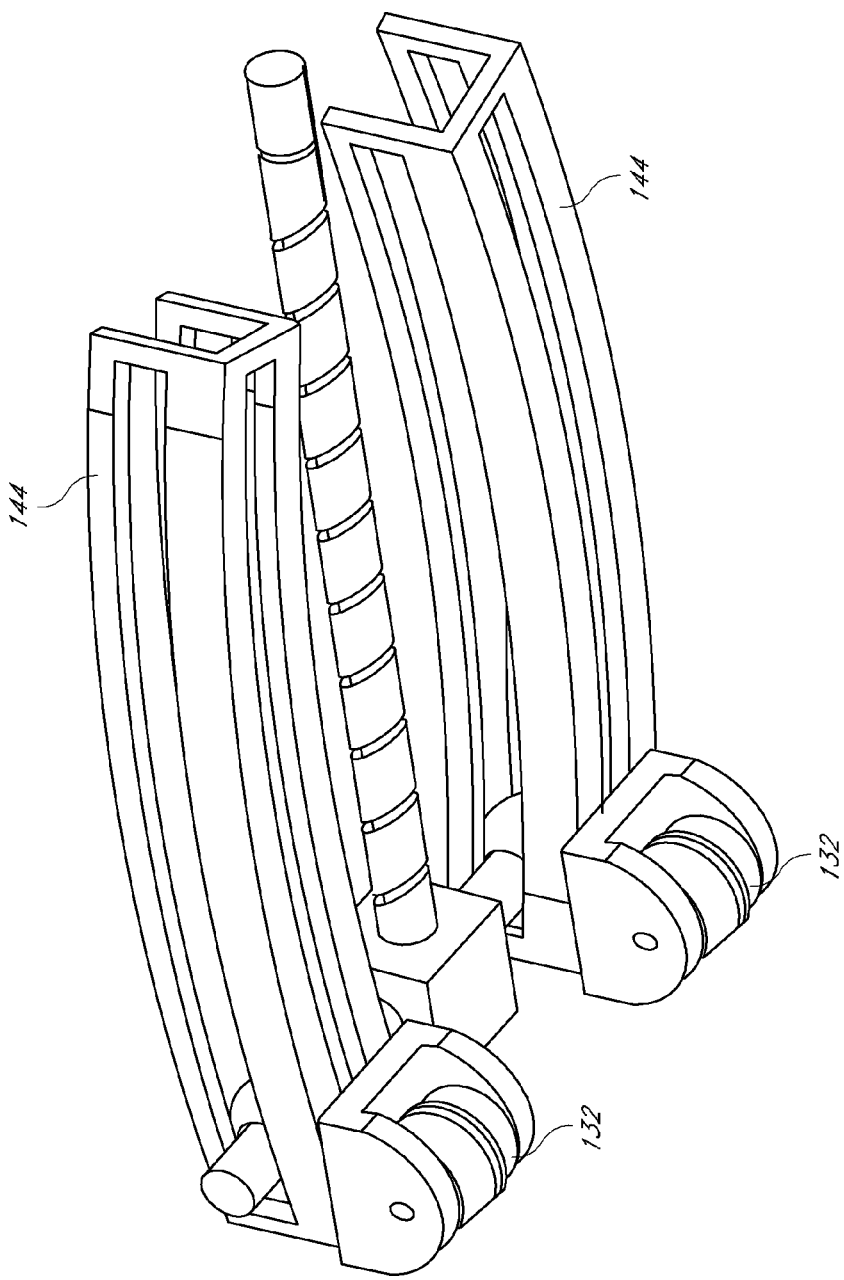
FIG. 8 is an illustration of the independent movement device, according to one embodiment of the invention.

FIG. 8 is a bottom perspective view illustration of the longitudinal movement mechanism 122 showing the first massage thumb 132A and second massage thumb 132B disposed below the tracks 144.

Programmable Therapeutic Device

Figure 9:
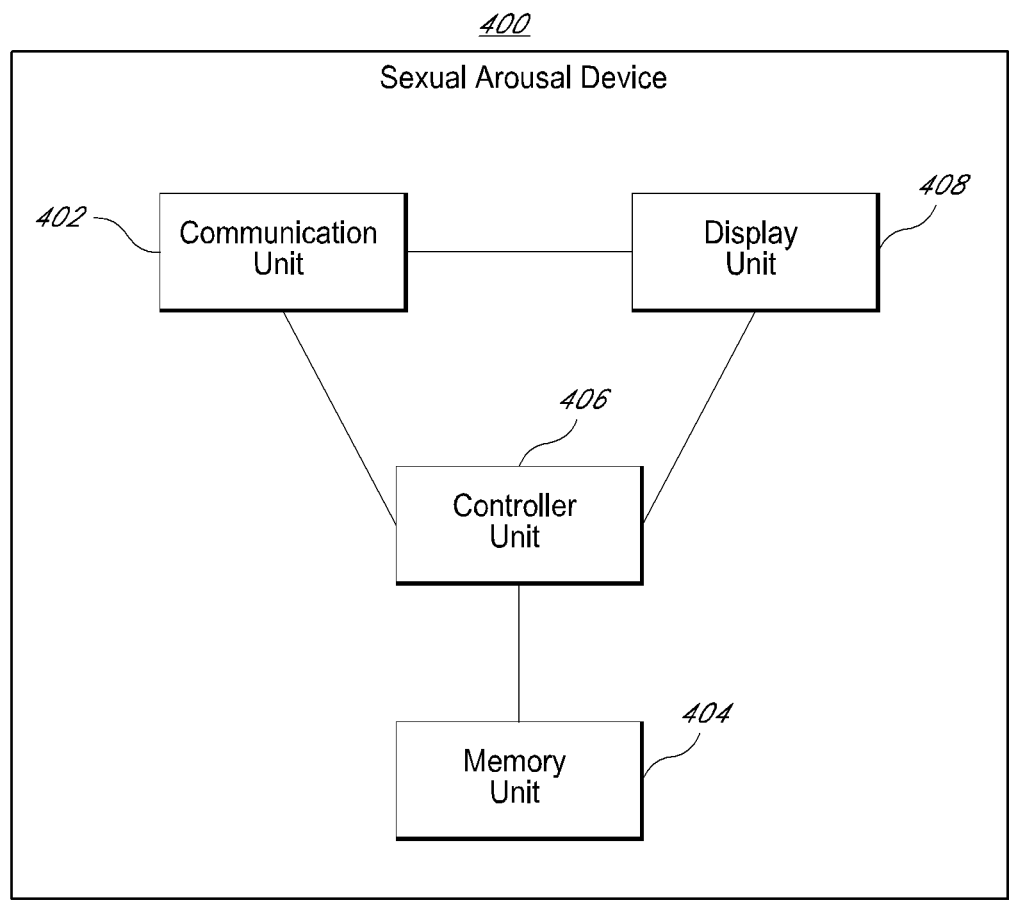
FIG. 9 illustrates a block diagram of the electronic components of the sexual stimulation device, according to one embodiment of the invention.

The sexual stimulation device can be electronically controlled and configured to transmit and receive data, as shown by the block diagram in FIG. 9. That is, the sexual stimulation device can transmit both control and informational data back to a device within a network as will be described in greater detail below. The sexual stimulation device 400 can include a communication unit 402 which transmits and receives data to an external device (see FIG. 10), a memory unit 404 which stores programming information and data on the usage of the device 400, and a controller unit 406 which sends commands to the other units. The memory unit 406 stores usage data relating to the timing and duration of use of oscillatory, vibratory, and/or suction elements as well as suction force, speed of the device, and intensity, for example. The controller unit 406 may be connected with the interactive controls and the various mechanical actuators described above, such as vibration motors, vacuum pumps, lubrication pumps, etc. in order to translate the user's inputs into actions by the sexual stimulation device. The controller unit 406 can also be connected with a display unit 408 which provides a visual and/or audible indication of the action being taken by the sexual stimulation device. In one embodiment, the controller unit 406 is a processor connected with memory in the memory unit 404, as will be further described below.

In one aspect of the invention, the sexual stimulation device can collect data and interpret and respond to this data. The sexual stimulation device can transmit internally generated and/or externally received data to other devices and systems within communications range. In another aspect of the invention, the sexual stimulation device is configured to measure the user's physiological response to stimuli to provide information to facilitate assessment of genital arousal. Genital arousal can be assessed, for example, by measuring one or more of the following physiological metrics: vasocongestion of genital tissues such as vaginal walls, clitoris, and labia, changes in temperature associated with increased blood flow to the vulva, changes in blood flow to vulvar tissues, blood pressure, heart rate, increased redness or darkening of genital tissue, and vaginal lubrication. Physiological responses can be measured using various sensors adapted for use with the sexual stimulation device. To measure vasocongestion, for example, the device can optionally include a sensor configured for vaginal photoplethysmography (VPG) or clitoral photoplethysmography (CPG) to measure changes in genital blood volume. Temperature can be measured with a thermometer sensor attached to the device. Blood flow changes in the vulvar tissues can be measured, for example, using a laser Doppler imaging (LDI) sensor in communication with the device. Measurement sensors collect, identify, display and/or communicate with a first computer as will be described in greater detail below. Additionally, audio-sensing controllers can generate control signals based on environmental sounds, music, voices, voice commands, etc.

The communication unit 406 can utilize a communication port (not shown) on the sexual stimulation device in order to communicate with an external device. The communication port optionally includes a removably attached waterproof plug to seal the port when not in use. The communication port can be a USB (Universal Serial Bus) cable, an Ethernet cable, a proprietary cable, or any other suitable cable or connector type. The cable or connector is designed to provide a sealable, waterproof connection in the event that the cable must be connected to the sexual stimulation device during operation. The cable or connector provides a data exchange port or gateway to a third party source through, for example, cloud technology. The connector is configured to initiate the device, download data, organize data, and to access the on-board memory or software of the device. The communication port also serves a dual purpose as a charging port to charge the battery within the device, as is known with the USB standard.

The memory unit 404 addresses all local/on board activities, diagnostic, programming, function selection, power usage, and intensity of each mode. Preferably, the memory unit 404 instructs the sending and receiving of data, including binary and others, from the device to and from third party sources such as a therapist, caregiver, service provider, etc. The memory unit 404 is adapted to allow the user to download, select, program, and retain a specific sequence or sequences of related, desired, required, prescribed, and/or selected therapeutic activities. Additionally, the memory unit 404 is configured to combine and integrate these activities into a time-defined experience. In another aspect, the memory unit 404 retains individual user profiles including therapeutic programs, power management, diagnostics such as troubleshooting, and storage/data collection of all activities. The information stored on the memory unity 404 can comprise a session or recipe of treatment protocols to be shared with another user, caregiver, or insurance provider.

USB data from the host computer can control the speed, intensity, and/or direction of the device motors directly, or with programmed control profiles for autonomous operation when the USB device is disconnected from the computer. The host computer can manage, arrange, control, navigate, adjust, and program the desired activity of the device. As used herein, "activity" can refer to power, speed, torque, duration, sequencing, intensity and function. The control profile includes a script with a sequence of instructions to drive the various electro-mechanical operations of the device. The script is stored as a file which can be edited in the host computer and loaded into the device via the connector or cable, for example. A library of user preference files and/or medical treatment protocols particular to the user can be created to store a variety of therapy profiles to suit the needs and preferences of the user and prescribed protocol of a care giver, such as a physician or therapist. The host-side application can show, for example, a graphic of the vulva with the three modes of stimulation overlaid for programming purposes. Other music and graphics can be included here to enhance the patient's/user's experience if the live application is run concurrently with the operation of the device handset.

In another embodiment, the communication port is a wireless transmission unit which transmits data wirelessly to another device, as will be described further below. A wireless transceiver can be attached to a computer such as a personal computer, portable computer, networked computer, or handheld computer, or to a communication device or other electronic device via a USB, parallel, serial, or other input/output port. This transceiver can then be used to receive and send signals to and from the network. Signals generated by a computer or other device can be: GUI (graphical user interface), programs which can provide users with sophisticated computer interfaces for generating fine GUI-based interaction with the device. User programmed signals useable to interact with the device can be created, used and stored. These signals can also be shared, embedded in devices, or sold online or through other outlets. Special media played on a computer or other device can be encoded with a control track that causes the device to behave in synchronization with the media being viewed or heard. Additionally, the media could itself be controlled or altered in response to signals received from the network. Standard media, without a pre-programmed control track, played on a computer or other device, could be interpreted by software, firmware, or hardware and used to cause the sexual stimulation device to behave in synchronization with the media being viewed or heard.

In still other embodiments, commercially available media such as video game ROMS, audio and/or video CDs and DVDs, and electronic MP3, MPEG and other electronic media files can be encoded with a special control signal track that is extracted and broadcast by a compatible wireless controller connected to the standard outputs of a playback device. The media control signal track can thus be transmitted to cause the sexual stimulation device to behave in synchronization with the music, video or other material being viewed and/or listened to without requiring a specialized media player. In one exemplary embodiment, an encoded control signal in an MPEG or other digital video file can be outputted, for example through a port such as a headphone connector or other output port, to a wireless compatible transmitter for controlling the sexual stimulation device in a desired synchronization with the media content. Pagers, cellular phones and other portable, compatible communications devices can be used to generate control signals, remotely controlling the sexual stimulation device directly and/or through existing national and international communication networks. In one aspect of the invention, through software enhanced manipulation, the device will receive a medium impulse and translate the medium into a controllable/volumetric vibrating pulse. As used herein, "medium" includes, without limitation, music, video input, holography, etc. As will be appreciated by a skilled artisan, any number of software programs can be utilized to create synchronicity between the device and the medium. The program advantageously assigns a value to reflect, synchronize, and organize for example, the quality, intensity, and frequency of the oscillation, vibration, and/or suction features of the device. The device is configured to collect, access audio/video information via the connector or cable such as the USB port. The memory unit 404 in turn accepts, analyzes, organizes, and selectively redeploys the selected and/or prescribed usage data relating to, for example, pulsation and/or vibration information based on a specific, individually tailored therapy program, desired effect, or personal value system, as will be further detailed below.

Figure 10:
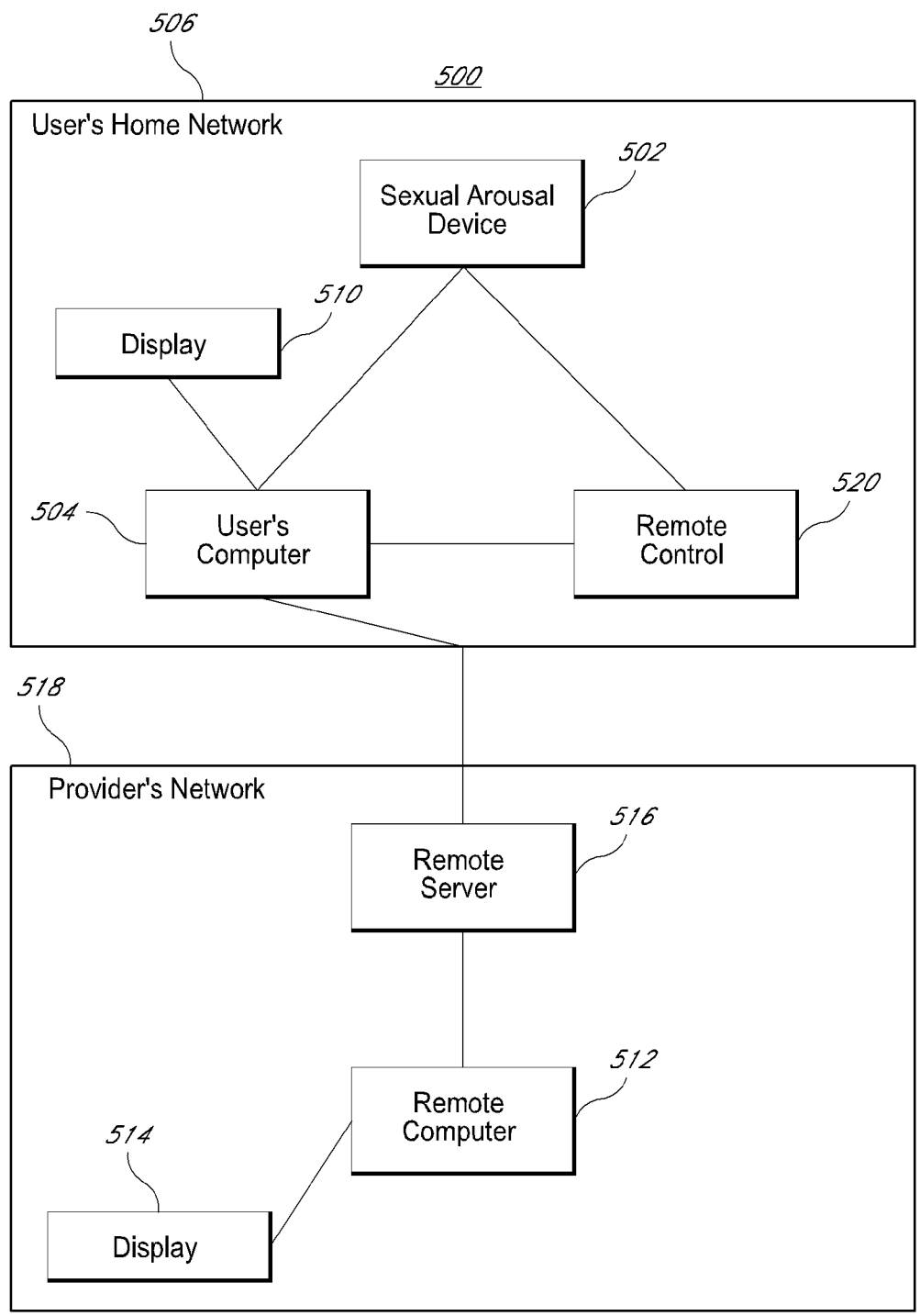
FIG. 10 illustrates a block diagram of a system for interactive treatment of a female sexual disorder, according to one embodiment of the invention.

One aspect of the invention provides a system for treating female sexual dysfunction. As illustrated in FIG. 10, the system includes a sexual stimulation device 502 and an external device which is in communication with the sexual stimulation device 502. It will be appreciated that the external device can include mobile devices such as smartphones, tablet PCs, iTouch® as well as desktop computers and/or laptops. As illustrated, the external device can be a home computer 504. The home computer 504 can be connected with the sexual stimulation device 502 via a wire, such as a USB (Universal Serial Bus) or Ethernet cable, or wirelessly through an appropriate wireless transmission protocol, such as Wireless USB, Bluetooth®, Wi-Fi, ZigBee®, 802.11 standard, or any standard, non-standard, or proprietary wireless protocol can be used for this purpose. The home computer 504 and sexual stimulation device 502 can therefore be encompassed within a network 506, such as a user's home network 508, so that the computer 504 and sexual stimulation device 502 can easily communicate.

The home computer 504 is configured to communicate with the sexual stimulation device 502 in order to receive data from the sexual stimulation device 502 and transmit data to the sexual stimulation device 502. The home computer 504 receives usage data on how the sexual stimulation device 502 is being used, including the amount of time the device is being used and the particular settings or features of the sexual stimulation device that are being activated by the user. In particular, the home computer 504 can receive usage data relating to the duration of use, user's implementation and timing of the oscillatory, vibrational, and/or suction elements, preferred intensity, oscillatory directionality, utilization of heating or cooling elements and/or lubricants, as well as dispensing of medicaments. Additionally, the sexual stimulation device 502 can also transmit other information, such as the status of a battery or the behavior of other components of the sexual stimulation device as has already been described above.

The home computer 504 can also transmit information to the sexual stimulation device 502, such as a program which will carry out a specific function on the sexual stimulation device. The program can be a sequence of actions by one or more of the mechanical or electronic features of the sexual stimulation device. In one embodiment, customized programs are written for each user based on the user's preferences or the user's profile. The user can interact with the computer through and attached display 510 or a variety of other input devices. The preferences and profile of the user can be determined based on the data provided by the sexual stimulation device on how the user has previously used the device. The user may also be able to create a customized program on the computer using software created to interact with the sexual stimulation device 502.

The customized program is created in conjunction with external stimulation, such as audio or visual media. For example, the program can be written to correspond to music, so that the function of the sexual stimulation device changes as the rhythm, volume or style of the music changes. Exemplary systems for translating an audio signal into a control signal to generate a particular tactile sensation such as synchronized vibration include the control system described in U.S. Pat. No. 5,684,722, the entire contents of which are hereby incorporated by reference. In one aspect of the invention, the device is in communication with a music player such as an MP3 player, iPod®, or other musical device and the vibratory, vacuum, and/or oscillatory element are programmed to synch with a music composition while simultaneously allowing the user to audibly enjoy appreciation of the musical composition. This may be provided for by placing a speaker, with suitable housing to allow full function of the speaker including transmission of vibratory sound waves, within the device. With this arrangement the user may audibly enjoy the music permeating from the device while simultaneously enjoying the rhythmic vibration and/or oscillation of the music transferred through the device. Speakers may be selectively positioned within the housing and may include a vibratory feature. In one embodiment, the speakers are piezoelectric.

Visual media could, for example, have images ranked so that the value of the ranking corresponds to a level or type of action by the sexual stimulation device. The user can also be able to have a customized program coincide with pictures or videos in the same manner, so that the behavior of the sexual stimulation device changes depending on the pictures shown. The visual media may be displayed on the display unit 510 connected with the computer 502. In another embodiment, even written content, such as a poem or letter, could be corresponded to certain device functions. The functions of the sexual stimulation device could be altered based on certain words, certain patterns of words or based on separate ranking or rating of the content. In yet another embodiment, the customized program can include code and signal processing/image display systems for displaying one or more images using holographic techniques such as those techniques described in, for example, U.S. Pat. No. 8,294,749, the contents of which are hereby incorporated by reference in their entirety.

In another aspect, the user may operate the sexual stimulation device in a "manual" mode during the presentation of audio or visual media. In this situation, the data on how the sexual stimulation device is used may be beneficial to a therapist, health care professional or even the user in order to determine if certain audio or visual media causes arousal. The data on the use of the sexual arousal and which audio or visual media is being displayed can be coordinated at the computer if, for example, the computer is presenting the audio or visual media and also receiving data from the sexual stimulation device.

In one embodiment, a therapist or other healthcare professional can create a program based on the healthcare professional's evaluation of the user. The program could be designed based on the user's progress in therapy or based on usage data of the sexual stimulation device received and analyzed by the healthcare professional. The system described in FIG. 10 therefore may include a remote computer 512 with a display 514 which will receive data from the sexual stimulation device 502 for use by a third party other than the user. [The sexual stimulation device 502 may upload data to the home computer 504 used by the user, and the user's computer 504 may then upload the data to a remote server 516 on a second network 518, such as that of the provider, which will then be downloaded by the third party for analysis and treatment of the user.

In another embodiment, the data may be uploaded to the remote server 516 for automated analysis using data collected from other users or data known as a standard for female arousal and behavior. The user may provide direct feedback via software on the home computer 504, and this feedback may be combined with usage data to, determine future programs which can better treat the user. The user feedback may also be transmitted to a therapist or healthcare professional for use in treatment sessions or for the healthcare professional to create new programs.

The system may also include a remote control device 520 which remotely operates the sexual stimulation device 502. The remote control device 520 may be provided simply for convenience of the user so the user can use one hand to keep the sexual stimulation device 502 positioned on the clitoris and the other hand to control the mechanical and electronic features of the sexual stimulation device 502 through the remote control 520. The remote control 520 may be connected with the sexual stimulation device wirelessly using infrared (IR), radio frequency (RF), Bluetooth® or 802.11 wireless protocols, although this list is not limiting. The remote control may be a proprietary remote control device designed specifically for the sexual stimulation device, or it could be another portable computer device, such as a smartphone, tablet computer, netbook or laptop. The remote control device could also be an input device on the user's computer, such as a mouse or keyboard. In another aspect, the sexual stimulation device 502 could be remotely controlled in real-time by the therapist or healthcare professional, such as via the remote computer 512. The therapist can then see the user's reaction to various types of stimuli in real-time and adjust the function of the sexual stimulation device 502 in real-time to more quickly improve the treatment for the user.

The system may also transmit data relating to the use of the sexual stimulation device to a health care provider or therapist for clinical or insurance purposes, which may provide avenues for reimbursement and insurance coverage of the costs associated with the purchase, use and treatment with the sexual stimulation device. The interaction that the user and the healthcare provider have with the device will improve the ability of the device and the healthcare provider to treat female sexual disorders by, for example, promoting bidirectional communication between both the device and the healthcare provider as well as between the patient/user and the healthcare provider. Additionally, the sexual stimulation device provides for the development of user-specific programs based on treatment protocols as well as usage data to specifically target patient conditions associated with female sexual dysfunction as will be described below with reference to FIGS. 11 and 12.

Methods/or Therapeutic Treatment

Figure 11:
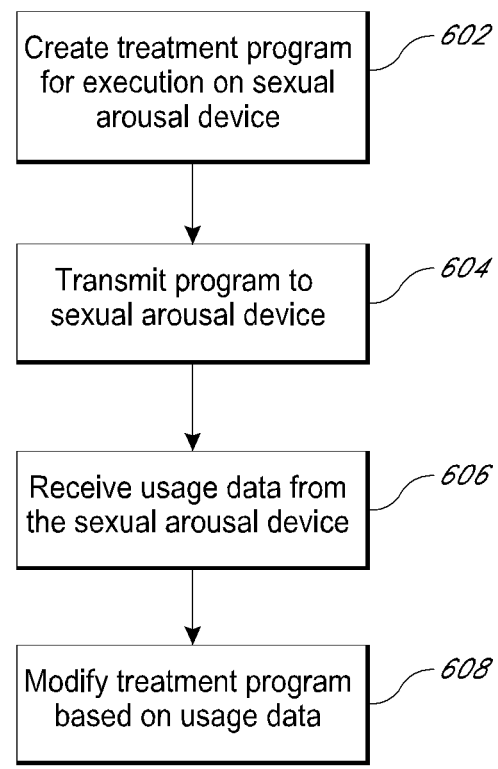
FIG. 11 is a flow chart illustrating an additional method of treatment of a female sexual disorder, according to one embodiment of the invention.

In one embodiment illustrated in FIG. 11, a method for treating a female sexual disorder in accordance with the aforementioned system is described. In step 602, a treatment program is created for executing on the sexual stimulation device. The treatment program may be a series of actions which the sexual stimulation device will carry out when the user initiates the program. As previously described, the program may be specifically designed by the user or a health care professional based on information about the user, the user's previous treatments or the user's progress through a series of treatments. In step 604, the program is transmitted to the sexual stimulation device for execution by the user. In step 606, the usage data from the sexual stimulation device is transmitted from the sexual stimulation device to the user's home computer, a remote server or a remote computer. In step 608, the usage data can be analyzed by the user, a healthcare professional or even an algorithm to determine the effectiveness of the treatment program and modify the program for future treatment sessions. The modifications may include altering the type of features of the sexual stimulation device which are utilized, or related audio or visual stimuli that are associated with the program. The modifications are made to reach treatment goals of the user and health care professional. Treatment goals, as used herein, include, without limitation, improvement in sexual desire/interest, improved feelings of sexual arousal, enhanced vulvar swelling, improved vaginal lubrication, enhanced orgasmic potential, improved orgasmic sensation and intensity, and reduction in dyspareunia.

Computer System

Figure 12:
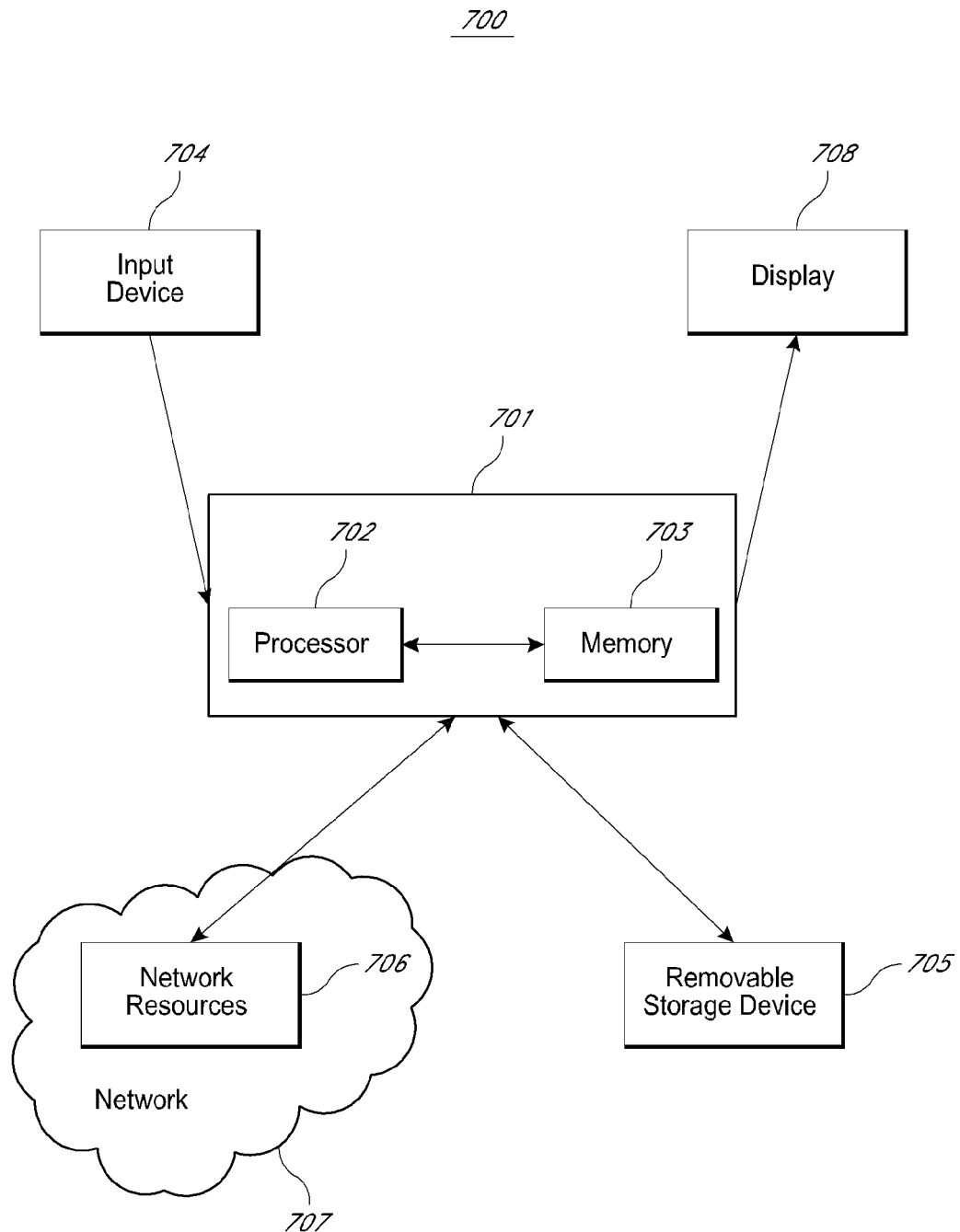
FIG. 12 is a block diagram that illustrates an embodiment of a computer/server system upon which an embodiment of the inventive methodology may be implemented.

FIG. 12 is a block diagram that illustrates an embodiment of a computer/server system 700 upon which an embodiment of the inventive methodology may be implemented. The system 700 includes a computer/server platform 701 including a processor 702 and memory 703 which operate to execute instructions, as known to one of skill in the art. The term "computer-readable storage medium" as used herein refers to any tangible medium, such as a disk or semiconductor memory, that participates in providing instructions to processor 702 for execution. Additionally, the computer platform 701 receives input from a plurality of input devices 704, such as a keyboard, mouse, touch device or verbal command. The computer platform 701 may additionally be connected to a removable storage device 705, such as a portable hard drive, optical media (CD or DVD), disk media or any other tangible medium from which a computer can read executable code. The computer platform may further be connected to network resources 706 which connect to the Internet or other components of a local public or private network. The network resources 706 may provide instructions and data to the computer platform from a remote location on a network 707. The connections to the network resources 706 may be via wireless protocols, such as the 802.11 standards, Bluetooth® or cellular protocols, or via physical transmission media, such as cables or fiber optics. The network resources may include storage devices for storing data and executable instructions at a location separate from the computer platform 701. The computer interacts with a display 708 to output data and other information to a user, as well as to request additional instructions and input from the user. The display 708 may therefore further act as an input device 704 for interacting with a user.

The above description of disclosed embodiments is provided to enable any person skilled in the art to make or use the invention. Various modifications to the embodiments will be readily apparent to those skilled in the art; the generic principles defined herein can be applied to other embodiments without departing from spirit or scope of the invention. Thus, the invention is not intended to be limited to the embodiments shown herein but is to be accorded the widest scope consistent with the principles and novel features disclosed herein.

What is claimed is:

1. A sexual stimulation system, comprising:
   a sexual stimulation device comprising:
   a housing having a rigid top portion and a flexible bottom portion;
   an oscillatory element comprising massage thumbs supported by a plurality of rollers, a vibratory element, a suction element, a lighting element and a plurality of interactive controls on the surface of said top portion of said housing, wherein said interactive controls are configured to allow a user of said device to interact with and modify the behavior of said sexual stimulation device;
   a first computer in communication with the sexual stimulation device which receives usage data from the sexual stimulation device pertaining to a use of the sexual stimulation device by a user; and
   a remote computer which receives the usage data from the first computer, wherein a program is created on the remote computer for execution on the sexual stimulation device which is based upon the usage data.

2. The system of claim 1, wherein the lighting element is an LED lighting element.

3. The system of claim 2, wherein said usage data is received by a health care provider.

4. The system of claim 3, wherein said usage data is translated to a treatment protocol which controls one or more of said vibratory element, oscillatory element, and suction element.

5. The system of claim 2, wherein said elements are independently operable;

and wherein said elements generate usage data.

6. The system of claim 1, wherein said device further comprises:

a wireless controller; and an interchangeable port.

7. The system of claim 6, wherein said device further comprises an actuator attached to said interchangeable port.

8. The system of claim 7, wherein said actuator is selected from the group consisting of a heating element, a lubricant dispenser, a medicament dispenser, and a finger-shaped tip configured for sexual stimulation.

9. The system of claim 6, wherein said wireless controller is configured for wireless communication with a device selected from the group consisting of a video game, audio device, video device, MP3 player, and smart phone.

10. The system of claim 6, wherein said wireless controller is configured to receive a medium impulse selected from the group consisting of music, video input, and holography.

* * * * *